US005733781A

United States Patent [19]
Ryder et al.

[11] Patent Number: 5,733,781
[45] Date of Patent: Mar. 31, 1998

[54] OLIGONUCLEOTIDES AND METHODS FOR INHIBITING PROPAGATION OF HUMAN IMMUNODEFICIENCY VIRUS

[75] Inventors: Thomas B. Ryder, Escondido; Theodore Jesse Kwoh, Carlsbad, both of Calif.

[73] Assignee: Gen-Probe Incorporated, San Diego, Calif.

[21] Appl. No.: 277,857

[22] Filed: Jul. 19, 1994

[51] Int. Cl.$^6$ .............................. C12N 5/22; C07H 21/00
[52] U.S. Cl. .................................. 435/325; 536/24.5
[58] Field of Search .......................... 435/5, 6, 948, 435/238, 325, 375; 514/44; 536/23.1, 24.1, 24.3, 24.5

[56] References Cited

U.S. PATENT DOCUMENTS

| | | | |
|---|---|---|---|
| 4,689,320 | 8/1987 | Kaji | 514/44 |
| 4,806,463 | 2/1989 | Goodchild et al. | 435/5 |
| 5,023,243 | 6/1991 | Tullis | 514/44 |
| 5,110,802 | 5/1992 | Cantin et al. | 514/44 |
| 5,144,019 | 9/1992 | Rossi et al. | 536/23.1 |
| 5,166,195 | 11/1992 | Ecker | 514/44 |
| 5,226,326 | 7/1993 | Bresser et al. | 435/6 |
| 5,264,423 | 11/1993 | Cohen et al. | 514/44 |
| 5,585,479 | 12/1996 | Hoke et al. | 536/24.5 |

FOREIGN PATENT DOCUMENTS

| | | |
|---|---|---|
| 0300687 | 7/1988 | European Pat. Off. . |
| 0339569 | 4/1989 | European Pat. Off. . |
| 0339569 | 11/1989 | European Pat. Off. . |
| 0403333 | 12/1990 | European Pat. Off. . |
| 0178978 | 2/1991 | European Pat. Off. . |
| 0516540 | 12/1992 | European Pat. Off. . |
| 0617132 | 3/1994 | European Pat. Off. . |
| 8505636 | 12/1985 | WIPO . |
| 8701211 | 12/1987 | WIPO . |
| 8707300 | 12/1987 | WIPO . |
| 8810300 | 12/1988 | WIPO . |
| 91/10746 | 7/1991 | WIPO . |
| 9216180 | 10/1992 | WIPO . |
| 9313223 | 7/1993 | WIPO . |
| 9408004 | 4/1994 | WIPO . |

OTHER PUBLICATIONS

Agrawal et al. "Oligondeoxynucleoside phosphoramidates and phosphorothioates as inhibitors of human immunodeficiency virus" Proc. Natl. Acad. Sci. USA 85: 7079–7083, Oct. 1988.

Ratner et al. Complete Nucleotide Sequence of the AIDS Virus, HTLV–III. Nature 313, 277–284, Jan. 1985.

Hélèn and Toulmé, "Specific Regulation Of Gene Expression by Antisense, Sence and Antigene Nucleic Acids," *Chemica et Biophysica Acta* 1049:99–125 (1990).

Uhlmann and Peyman, "Antisense Oligonucleotides: A New Therapeutic Principle," *Chemical Reviews* 90:544–584 (1990).

Majumdar et al., "Stepwise Mechanism of HIV Reverse Transcriptase: Primer Function of Phosphorothioate Oligodeoxynucleotide," *Biochemistry* 28:1340–1346 (1989).

Matsukura et al., "Regulation of Viral Expression of Human Immunodeficiency Virus In Vitro by an Antisense Phosphorothioate Oligodeoxynucleotide Against rev (art/trs) in Chronically Infected Cells," *Proc. Natl. Acad. Sci. USA* 86:4244–4248 (1989).

Juliano and Akhtar, "Liposomes as a Drug Delivery System for Antisense Oligonucleotides," *Antisense Research and Development* 2:165–176 (1992).

Kinchington et al., "A comparison of gag, pol and rev antisense oligodeoxynucleotides as inhibitors of HIV–1," *Antiviral Research* 17:53–62 (1992).

Rhodes and James, "Inhibition of human immunodeficiency virus replication in cell culture by endogenously synthesized antisense RNA," *Journal of General Virology* 71:1965–1974 (1990).

Schwartz et al., "Cloning and Functional Analysis of Multiply Spliced mRNA Species of Human Immuodeficiency Virus Type I," *Journal of Virology* 64:2519–2529 (1990).

Sullivan et al., "Inhibition of Human Immunodeficiency Virus–1 Proliferation by Liposome–Encapsulated Sense DNA to the 5' TAT Splice Acceptor Site," *Antisense Research and Development* 2:187–197 (1992).

Vaishnav and Wong–Staal, "The Biochemistry of Aids," *Annu. Rev. Biochem.* 60:577–630 (1991).

Weislow et al., "New Soluble–Formazan Assay for HIV–1 Cytopathic Effects: Application to High–Flux Screening of Synthetic and Nature Products for AIDS–Antiviral Activity," *J. Natl. Cancer. Inst.* 81:577–586 (1989).

*Primary Examiner*—James Ketter
*Assistant Examiner*—Thomas G. Larson
*Attorney, Agent, or Firm*—Lyon & Lyon LLP

[57] ABSTRACT

The present invention concerns the use of oligonucleotides to inhibit propagation of human immunodeficiency virus (HIV). Preferred HIV target sites are identified and oligonucleotides designed to hybridize to a target site, or be analogous to a target site, are described. The preferred use of the oligonucleotides is to inhibit HIV propagation in a patient infected with HIV.

104 Claims, 4 Drawing Sheets

OLIGONUCLEOTIDES AND METHODS FOR INHIBITING PROPAGATION OF HUMAN IMMUNODEFICIENCY VIRUS

FIELD OF INVENTION

The present invention features compounds and methods for inhibiting propagation of human immunodeficiency virus.

BACKGROUND OF THE INVENTION

Oligonucleotides such as antisense oligonucleotides can hybridize to a target RNA, such as mRNA, and inhibit protein production from that RNA. Numerous mechanisms have been proposed to explain the effects of antisense oligonucleotides. For example, see Helene, C. and Toulme, J. Biochimica et Biophysica Acta 1049:99 (1990), and Uhlmann, E. and Peyman, A. Chemical Reviews 90:543 (1990). Proposed mechanisms include forming a DNA: RNA substrate for cellular RNase H, hybridization of an antisense oligonucleotide to nascent mRNA leading to premature transcription termination and interfering with mRNA processing by hybridizing to a pre-mRNA intron/exon junction. These and several other proposed mechanisms for inhibiting nucleic acid activity by antisense oligonucleotides are based upon the ability of antisense oligonucleotides to hybridize to a target nucleic acid sequence.

Tullis, U.S. Pat. No. 5,023,243, provides a general description of using antisense oligonucleotides to inhibit protein translation. Kaji, U.S. Pat. No. 4,689,320, provides data showing a decrease in mortality in mice infected with Herpes Simplex Virus by administering an antisense oligonucleotide targeted to herpes simplex virus. Goodchild et al., U.S. Pat. No. 4,806,463, provides data concerning the ability of antisense oligonucleotides to inhibit HTLV-III (HIV) replication and gene expression in cultured cells infected with HIV. Cantin et al., U.S. Pat. No. 5,110,802, describe the use of a methylphosphonate-linked oligonucleotide to inhibit HIV replication. These U.S. patents are hereby incorporated by reference herein. Matsukura et al., Proc. Natl. Acad. Sci. 86:4244 (1989) describe inhibiting HIV expression using a phosphorothioate-linked oligonucleotide targeted to a rev nucleotide sequence.

Oligonucleotides having nucleic acid sequences complementary to HIV nucleic acid regions are mentioned in references such as Moncany and Montagnier, EPO 0 403 333 A2 (published 1990); Sauvaigo and Fouque EPO 0 516 540 A1 (published 1992); Alizon et al., PCT/EP85/00487; Gingeras et al., PCT/US92/02037; and Irvine et al., PCT/US92/11168.

SUMMARY OF THE INVENTION

The present invention features compounds and methods for inhibiting propagation of human immunodeficiency virus (HIV). Preferred HIV target sites are identified and oligonucleotides designed to hybridize to a target site, or be analogous to a target site, are described. The preferred use of the oligonucleotides is as an anti-HIV agent to inhibit HIV propagation in a patient infected with HIV. Other uses of the present invention include detecting the presence of HIV by using the oligonucleotides as detection probes or amplification primers, and measuring the ability of an oligonucleotide to inhibit HIV propagation to evaluate its suitability as an anti-HIV agent for a strain of HIV or to diagnose the presence of HIV in a patient.

The oligonucleotides of the present invention are based on the following preferred anti-HIV nucleic acid sequences:

SEQ. ID. NO. 1: ATTCCTTTGT GTGCTGGTAC CCATGC,

SEQ. ID. NO. 2: CCTCCAATTC CTTTGTGTGC TGGTAC,

SEQ. ID. NO. 3: GCTGGTGATC CTTTCCATCC CTGTGG,

SEQ. ID. NO. 4: CTCCTTGACT TTGGGGATTG TAGGG,

SEQ. ID. NO. 5: CTACTACTCC TTGACTTTGG GGATTG,

SEQ. ID. NO. 6: CCTCTGTTAG TAACATATCC TGCTTTTCC,

SEQ. ID. NO. 7: CCCACTCCAT CCAGGTCATG TTATTCC,

SEQ. ID. NO. 8: GGTTGCTTCC TTCCTCTCTG GTACCC

SEQ. ID. NO. 9: CCATTCATTG TGTGGCTCCC TCTGTGG,

SEQ. ID. NO. 10: CTAGCAGTGG CGCCCGAACA GGTTCGCCTG TTCGGGCGCC A,

SEQ. ID. NO. 11: CCCCCGCTTA ATACTGACGC TCTCGC,

SEQ. ID. NO. 12: CGATCTAATT CTCCCCCGCT TAATACTG,

SEQ. ID. NO. 13: CAGTATTAAG CGGGGGAGAA TTAGATCG,

SEQ. ID. NO. 14: CCTGTACCGT CAGCGTCATT,

SEQ. ID. NO. 15: GTCTGGCCTG TACCGTCAGC GTCATT,

SEQ. ID. NO. 16: GCCTCAATAG CCCTCAGCAA ATTGTT,

SEQ. ID. NO. 17: ATCTTTCCAC AGCCAGGATT CTT,

SEQ. ID. NO. 18: TCCTGGATGC TTCCAGGGCT CTAGTC,

SEQ. ID. NO. 19: TCCTGGATGC TTCCAGGGCT C,

SEQ. ID. NO. 20: GACTTCCTGG ATGCTTCCAG GGCTC,

SEQ. ID. NO. 21: CTCTCCTTTC TCCATTATCA TTCTCCCGC,

SEQ. ID. NO. 22: CATCACCTGC CATCTGTTTT CCATAATCCC,

SEQ. ID. NO. 23: CCTGTCTACT TGCCACACAA TCATCACCTG C,

SEQ. ID. NO. 24: GCTACTATTG CTACTATTGG TATAGGTTGC, and

SEQ. ID. NO. 25: ACTATTGCTA TTATTATTGC TACTACTAAT.

Oligonucleotides having nucleic acid sequences substantially corresponding to a preferred nucleic acid sequence and consisting essentially of the preferred nucleic acid sequence are also covered by the present invention.

"Substantially corresponding" refers to an oligonucleotide having a nucleic acid sequence which is identical to, or has no more than a 20% nucleotide base difference (excluding RNA or DNA equivalent nucleotides), from a specified sequence and has the claimed activity (e.g., anti-HIV activity). The nucleotide differences include mismatches, internal additions, internal deletions, and/or outside deletions. In addition, additional nucleotides outside of the specified sequence may be present. The additional nucleotides may be complementary or non-complementary to HIV nucleic acid. Preferably, the substantially corresponding sequence differs by no more than 10%, more preferably no more than 5% from the specified sequence.

"Consisting essentially" of a nucleic acid sequence means the oligonucleotide contains a nucleic acid sequence which has 0 to 10%, preferably 0 to 5% nucleotide base difference (excluding RNA or DNA equivalent nucleotides), from the specified nucleotide sequence and has the claimed activity (e.g., anti-HIV activity). Nucleotide differences include mismatches, internal additions and/or internal deletions. In addition "consisting essentially" also provides a size limitation of up to 4 additional nucleotides or up to two outside deletions. The additional nucleotides may be complementary, or non-complementary, to HIV nucleic acid.

"RNA and DNA equivalents" refer to RNA and DNA molecules having the same complementary base pair hybridization properties. RNA and DNA equivalents have different sugar groups (i.e., ribose versus deoxyribose), and may differ by the presence of uracil in RNA and thymine in DNA. The difference between RNA and DNA equivalents do not contribute to differences in substantially corresponding nucleic acid sequences because the equivalents have the same degree of complementarity to a particular sequence.

When used as an anti-HIV agent, oligonucleotides of the present invention are preferably made up of deoxynucleotides. A DNA oligonucleotide may be more effective in inhibiting HIV than its RNA equivalent, because a DNA oligonucleotide can form a DNA:HIV RNA duplex where the HIV RNA is degraded by a RNase H activity.

Thus, a first aspect of the present invention describes an isolated oligonucleotide able to inhibit propagation of HIV in vivo or in vitro. The oligonucleotide is 18 to 100 nucleotides in length having a nucleic acid sequence substantially corresponding to a preferred nucleic acid sequence.

"HIV propagation" refers to the overall multiplication of HIV, and includes intracellular multiplication of HIV proteins and nucleic acids and cellular infection by HIV virions and nucleic acids. HIV propagation can occur in vivo (i.e. in a patient), or in vitro (i.e., in cultured cells). HIV propagation can be measured, for example, by determining HIV p24 protein production in cultured cells infected with HIV.

Inhibition of HIV propagation results in a decrease, to some extent, in HIV propagation. Oligonucleotides able to inhibit HIV propagation in vivo or in vitro are useful in different aspects of the present invention. Preferably, the anti-HIV oligonucleotides have an in vitro $EC_{90}$ (concentration required to achieve 90% inhibition), as measured by the techniques described in the examples below, of 1,000 nM or less, more preferably 300 nM or less, more preferably 100 nM or less.

More preferred anti-HIV oligonucleotides have a high therapeutic index. The therapeutic index refers to the oligonucleotide concentration which inhibits cell growth divided by the oligonucleotide concentration which inhibits HIV propagation. The cytotoxic effect can be expressed in terms of $IC_{50}$ which is the oligonucleotide concentration required to achieve a 50% inhibition in cell count. The therapeutic index of anti-HIV oligonucleotides can be measured in vitro prior to use in vivo. Preferred anti-HIV oligonucleotides have an $IC_{50}/EC_{90}$ of greater than 5, more preferably greater than 20, more preferably greater than 35 as measured by the techniques described in the examples below.

An "isolated oligonucleotide" refers to an oligonucleotide in a form not found in nature without human intervention. Such oligonucleotides include oligonucleotides purified, to some extent, and recombined with foreign nucleic acid.

The preferred oligonucleotide contains at least 50% phosphorothioate linkages, more preferably more than 95% phosphorothioate linkages, joining the individual nucleotides. Examples are described employing oligonucleotide with 100% phosphorothioate linkages. The presence of phosphorothioate linkages provides for anti-HIV activity which is apparently independent of an anti-sense inhibitory mechanism.

Another aspect describes an isolated oligonucleotide 20 to 100 nucleotides in length having a nucleic acid sequence selected from the group of preferred nucleic acid sequences SEQ. ID. NOs. 1–18, 20–25 and RNA equivalents thereto, SEQ ID NOs: 26–43 and 45–50; and complements of the DNA and RNA equivalents, SEQ ID NOs: 52–69, 71–76, and 77–94 and 96–101.

Another aspect describes a therapeutic composition able to inhibit propagation of HIV in a patient. The composition contains a therapeutically effective amount of an isolated oligonucleotide 18 to 100 nucleotides in length having a nucleic acid sequence substantially corresponding to a preferred nucleic acid sequence. The composition also contains a pharmacologically compatible carrier.

A "therapeutically effective amount" is one which inhibits propagation of HIV in a patient infected with HIV. Preferably, the therapeutically effective amount relieves, to some extent, one or more symptom associated with HIV infection.

A "pharmacologically compatible carrier" is a formulation to which the oligonucleotide can be added to dissolve it or otherwise facilitate its administration to a patient. Examples of pharmacologically compatible carriers include water, saline, physiologically buffered saline, cyclodextrins, and cationic liposomes.

Another aspect describes a recombinant nucleic acid containing a transcription site operably linked to an oligonucleotide having a nucleic acid sequence substantially corresponding to a preferred nucleic acid sequence. By "operably linked" is meant that transcription of the anti-HIV oligonucleotide is to some extent under control of the transcription site. Uses of the recombinant nucleic acid include producing large quantities of oligonucleotides having a particular nucleic acid sequence, and to deliver oligonucleotides having a particular nucleic acid sequence into a cell infected with HIV.

Another aspect describes a method of inhibiting or decreasing propagation of HIV. The method involves contacting a cell with a HIV propagation decreasing effective amount of an oligonucleotide. The oligonucleotide has a nucleic acid sequence 18 to 100 nucleotides in length substantially corresponding to a preferred nucleic acid sequence. "A propagation decreasing effective amount" refers to an amount sufficient to inhibit propagation of HIV. The method is preferably used to inhibit HIV propagation in a patient.

Another aspect describes a method for treating a patient infected with HIV. The method involves administering to a patient a therapeutically effective amount of an oligonucleotide 18 to 100 nucleotides in length having a nucleic acid sequence substantially corresponding to a preferred nucleic acid sequence.

Other features and advantages of the invention are apparent from the following description of the preferred embodiments and the claims.

DESCRIPTION OF THE PREFERRED EMBODIMENTS

Figure 1A:
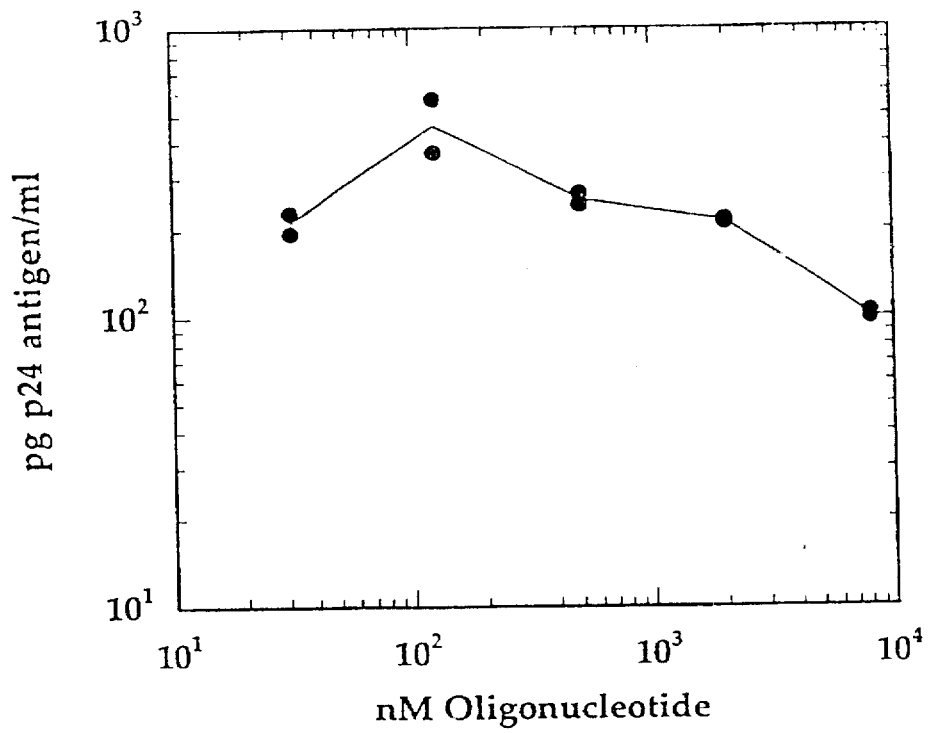
FIGS. 1A and 1B illustrate the ability of phosphorothioate oligonucleotide corresponding to SEQ. ID. NO. 2, to inhibit HIV gene expression in chronically infected cells.

The present invention concerns oligonucleotides targeted to the HIV genome. The oligonucleotides are designed to hybridize to a particular HIV nucleic acid sequence or to be analogous to a particular HIV nucleic acid sequence, and are preferably used to inhibit HIV propagation. The oligonucleotides have various uses relating to their ability to inhibit HIV propagation and/or hybridize to a HIV nucleic acid sequence. Such uses include use as a therapeutic agent and use in diagnostic assays.

The anti-HIV oligonucleotides can be used to inhibit HIV propagation alone or in combination with other anti-HIV oligonucleotide or anti-HIV treatments. For example, a first anti-HIV oligonucleotide can be used in combination with a second anti-HIV oligonucleotide. The second anti-HIV oligonucleotide may be either, 1) a subtargeted oligonucleotide, 2) a second separately targeted oligonucleotide, or 3) a non-targeted phosphorothioate oligonucleotide. A subtargeted oligonucleotide is designed to hybridize to a smaller region of the first targeted oligonucleotide target region. Thus, the nucleic acid sequence of a subtargeted oligonucleotide contains a truncated version of the nucleic acid of the targeted oligonucleotide. An example of a two separately targeted oligonucleotide combination is the phosphorothioate oligonucleotide of sequence SEQ ID NO:3 and the phosphorothioate oligonucleotide of SEQ ID NO:51, used in a ratio of about 1:1.

The following nucleic acid- sequences are provided:

SEQ. ID. NO. 1: ATTCCTTTGT GTGCTGGTAC CCATGC,

SEQ. ID. NO. 2: CCTCCAATTC CTTTGTGTGC TGGTAC,

SEQ. ID. NO. 3: GCTGGTGATC CTTTCCATCC CTGTGG,

SEQ. ID. NO. 4: CTCCTTGACT TTGGGGATTG TAGGG,

SEQ. ID. NO. 5: CTACTACTCC TTGACTTTGG GGATTG,

SEQ. ID. NO. 6: CCTCTGTTAG TAACATATCC TGCTTTTCC,

SEQ. ID. NO. 7: CCCACTCCAT CCAGGTCATG TTATTCC,

SEQ. ID. NO. 8: GGTTGCTTCC TTCCTCTCTG GTACCC,

SEQ. ID. NO. 9: CCATTCATTG TGTGGCTCCC TCTGTGG,

SEQ. ID. NO. 10: CTAGCAGTGG CGCCCGAACA GGTTCGCCTG TTCGGGCGCC A,

SEQ. ID. NO. 11: CCCCCGCTTA ATACTGACGC TCTCGC,

SEQ. ID. NO. 12: CGATCTAATT CTCCCCCGCT TAATACTG,

SEQ. ID. NO. 13: CAGTATTAAG CGGGGGAGAA TTAGATCG,

SEQ. ID. NO. 14: CCTGTACCGT CAGCGTCATT,

SEQ. ID. NO. 15: GTCTGGCCTG TACCGTCAGC GTCATT,

SEQ. ID. NO. 16: GCCTCAATAG CCCTCAGCAA ATTGTT,

SEQ. ID. NO. 17: ATCTTTCCAC AGCCAGGATT CTT,

SEQ. ID. NO. 18: TCCTGGATGC TTCCAGGGCT CTAGTC,

SEQ. ID. NO. 19: TCCTGGATGC TTCCAGGGCT C,

SEQ. ID. NO. 20: GACTTCCTGG ATGCTTCCAG GGCTC,

SEQ. ID. NO. 21: CTCTCCTTTC TCCATTATCA TTCTCCCGC,

SEQ. ID. NO. 22: CATCACCTGC CATCTGTTTT CCATAATCCC,

SEQ. ID. NO. 23: CCTGTCTACT TGCCACACAA TCATCACCTG C,

SEQ. ID. NO. 24: GCTACTATTG CTACTATTGG TATAGGTTGC, and

SEQ. ID. NO. 25: ACTATTGCTA TTATTATTGC TAC- TACTAAT.

Oligonucleotides containing these sequences, and containing sequences substantially corresponding to these sequences, are useful in one or more aspect of the present invention.

Preferred anti-HIV oligonucleotides contain the nucleotide sequence of an oligonucleotide which has been shown to have anti-HIV activity. The nucleotide sequence of a preferred anti-HIV oligonucleotide can be changed to obtain other useful anti-HIV oligonucleotides targeted to the same target site. Using present disclosure as a guide one skilled in the art can obtain useful variations of the preferred anti-HIV oligonucleotides.

Various possible mechanisms and examples are presented herein regarding the ability of oligonucleotides to inhibit HIV propagation. Unless otherwise stated in the claims these mechanisms and examples are not intended to limit the present invention but rather further illustrate and explain the present invention. The exact mechanism by which a particular oligonucleotide functions is expected to be a combination of different mechanisms.

I. INHIBITION OF HIV PROPAGATION

This section describes the design and use of anti-HIV oligonucleotides for treating a patient infected with HIV and for diagnosing the presence of HIV in a patient. After the initial design and testing of an oligonucleotide, additional testing can be carried out in vivo to further evaluate the oligonucleotide effectiveness. Tests can also be carried out to evaluate cellular oligonucleotide toxicity before proceeding to therapeutic administration. Thus, the present disclosure provides the necessary guidance to one skilled in the art to obtain oligonucleotides having anti-HIV activity, including oligonucleotides having a nucleic acid sequence substantially corresponding to a preferred nucleic acid sequence as discussed herein.

A. Oligonucleotide Design

Factors affecting an oligonucleotide's ability to inhibit HIV multiplication include oligonucleotide modifications, oligonucleotide size, and nucleic acid sequence. The importance of these factors can be initially determined in vitro, followed by in vivo studies.

1. Oligonucleotide Modification

Oligonucleotides can be modified to enhance their anti-HIV activity and therapeutic efficacy. Preferred modifications enhance oligonucleotide cellular uptake, oligonucleotide stability, and ability to inhibit HIV propagation. Modified oligonucleotides include oligonucleotide having a modified internucleotide linkage and/or a modified sugar group. Oligonucleotides can also have modified purine or pyrimidine bases which do not prevent the oligonucleotide from inhibiting HIV. Examples of modified internucleotide linkages include phosphorothioates, methylphosphonates, and phosphorodithioate. Examples of modified sugar groups include α-anomers and 2'-O-methyloligonucleotides. (Cantin and Woolf, *Trends in Microbiology* 1:270–276, 1993.)

Anti-HIV oligonucleotide preferably contain phosphorothioate linkages. Phosphorothioate linkages increase oligonucleotide stability, facilitate oligonucleotide uptake, and enable the oligonucleotide to inhibit HIV propagation by a mechanism which appears to be largely sequence independent. Thus, phosphorothioate linked oligonucleotides inhibit HIV by targeting, based on their nucleic acid sequence a specific HIV target site, and inhibit HIV by a mechanism not dependent on a specific sequence.

Oligonucleotides having phosphorothioate linkages inhibit viral reverse transcriptase, and may also inhibit gp120 binding to CD4 receptor and phosphorylating activity of PKC. The viral reverse transcriptase inhibitory effect increases as the size of the phosphorothioate oligonucleotide increases. Oligonucleotides having phosphorothioate linkages are described by Cohen et al., U.S. Pat. No. 5,264,423, and Kinchington et al., *Antiviral Research*, 17:53–62, 1992.

The cell association of phosphorothioate oligonucleotides, in experiments measuring oligonucleotide uptake and stability, was consistently ten times more than for phosphodiester oligonucleotides. Part of this effect appears to be due to greater cellular uptake of phosphorothioate oligonucleotides as compared to that of phosphodiester oligonucleotides, and part of the effect is attributed to increased phosphorothioate oligonucleotide stability. The difference in uptake mechanisms appears have a greater effect on cell association than the differences in oligonucleotide stability.

2. Oligonucleotide Size

The optimal oligonucleotide size should take into account different factors including different anti-HIV mechanisms and cellular uptake. Anti-HIV oligonucleotides are preferably 18 to 100 nucleotides in length and contain a preferred nucleic acid sequence, a nucleic acid sequence substantially corresponding to a preferred nucleic acid sequence, or a nucleic acid consisting essentially of a preferred nucleic acid sequence. Such oligonucleotides are targeted to an HIV target site. Additional nucleotides outside of complementary target region may be complementary to HIV nucleic acid or may be non-complementary. Anti-HIV oligonucleotides are preferably 18 to 50 nucleotides in length, more preferably, 20–35 nucleotides in length.

Oligonucleotides containing longer nucleic acid sequences of complementarity to a target sequence offer several advantages compared to shorter oligonucleotides, including increased target specificity and increased stability of the oligonucleotide:target duplex. The increased stability of the oligonucleotide:target duplex may facilitate the oligonucleotide nucleic acid inhibitory effect in different manners. For example, if the primary effect is translation arrest, the increased stability of the duplex could increase translation arrest by preventing a ribosome from displacing the oligonucleotide.

Another example of a possible mechanism involves degradation of the RNA strand of an DNA:RNA HIV duplex with an enzyme having RNase H activity. In this instance, the increased stability of the duplex increases the likelihood that the duplex is acted on by the ribonuclease. To be degraded by RNase H activity, the anti-HIV oligonucleotide in the DNA:RNA HIV duplex preferably contains three or more contiguous phosphodiester or phosphorothioate linkages.

Possible disadvantages of longer oligonucleotides include a decrease in oligonucleotide uptake and a possible increase in toxic effect. The degree of these effects are, at least in part, determined by the size of the oligonucleotide and types of oligonucleotide linkages. Possible toxic effects may be more pronounced, for example, using oligonucleotides containing phosphorothioate linkages.

3. Oligonucleotide Nucleic Acid Sequence

The oligonucleotides described herein are targeted to a target site as shown in Table 1.

TABLE 1

| SEQ. ID. NO. | HIV target Site | Sense (HIV RNA) |
|---|---|---|
| 1 | pol | Complementary |
| 2 | pol | Complementary |
| 3 | pol | Complementary |
| 4 | pol | Complementary |
| 5 | pol | Complementary |
| 6 | pol | Complementary |
| 7 | env | Complementary |
| 8 | env | Complementary |
| 9 | vpr | Complementary |
| 10 | lys-tRNA | Complementary and Analogous |
| 11 | gag | Complementary |
| 12 | gag | Complementary |
| 13 | gag | Analogous |
| 14 | RRE | Complementary |
| 15 | RRE | Complementary |
| 16 | RRE | Complementary |
| 17 | RRE | Complementary |
| 18 | tat | Complementary |
| 19 | tat | Complementary |
| 20 | tat | Complementary |
| 21 | tev | Complementrry |
| 22 | vir | Complementary |
| 23 | vif | Complementary |
| 24 | vpu | Complementary |
| 25 | vpu | Complementary |

Targeting is achieved by designing the oligonucleotide to be either complementary to an HIV target nucleic acid region, analogous to an HIV target nucleic acid sequence region, or both complementary and analogous to an HIV nucleic acid sequence region.

A complementary oligonucleotide has a nucleotide sequence enabling it to form stable hydrogen bonds with complementary nucleotides in the target sequence. For example, adenine forms hydrogen bonds with thymidine or uracil and guanine forms hydrogen bonds with cytosine. Thus, a complementary oligonucleotide is substantially complementary to its target sequence and preferably perfectly complementary to its target sequence.

"Substantially complementary to" a nucleic acid sequence means the oligonucleotide is capable of hybridizing to the nucleic acid sequence to form a detectable duplex and preferably has a 0 to 10%, more preferably 0 to 5%, nucleotide base difference (excluding RNA or DNA equivalent nucleotides), from a nucleic acid perfectly complementary to the nucleic acid sequence. Nucleotide base differences include mismatches, internal additions and/or internal deletions.

An analogous oligonucleotide has the same, or a functionally equivalent, nucleic acid sequence as its target region. Functionally equivalent nucleic acid sequences have the same complementary hydrogen bonding partners. For example, thymidine and uracil are functionally equivalent for complementary hydrogen bonding purposes.

Different target sites are targeted by the anti-HIV oligonucleotides. The different target sites encode different proteins having different functions, such as enzymatic, structural, and regulatory. Anti-HIV oligonucleotide complementary to their target site are expected to inhibit protein production encoded by the targeted nucleic acid.

As shown in Table 1, the following genes are targeted by complementary oligonucleotides: pol, env, vpr, gag, tat, tev, vir, vif, vpu. Additionally, due to the presence of overlapping exons, several genes in the HIV genome contain many of the same nucleic acid sequences in one or more reading frames. Schwartz et al., *Journal of Virology* 64:2519 (1990). Thus, reference to particular target site is not intended to exclude the possibility that more than one protein can be inhibited by a particular oligonucleotide.

The tev and tat genes code for regulatory proteins. The vif gene codes for a protein which is important for viral infectivity. The vpu gene codes for a protein which is believed to be necessary for normal availability of envelope proteins for virion assembly. The vpr gene codes for a protein involved in enhancement of gene expression and nuclear localization of HIV nucleic acids in the early stages of infection. The env and gag genes encode virion structural proteins including the receptor for virus-cell binding.

Several of the target sites may be involved in the production of more than one protein. The HIV genome has several open reading frames encoding precursor proteins. Moreover, during translation of some HIV mRNA the ribosome is thought to skip nucleotides thus generating different gene products. (Vaishnav and Wong-Stall *Annu. Rev. Biochem.* 60:577–630, 1991.)

HIV nucleic acid can encode polyproteins and precursor proteins. For example Pol, is made as a Gag-Pol polyprotein. Precursor proteins are cleaved to produce more than one protein. The pol gene encodes a precursor protein which is cleaved to yield three enzymes: a protease, reverse transcriptase, and an integrase. The gag gene encodes a precursor protein which is cleaved to yield three enzymes: a matrix protein, a capsid protein, and an HIV RNA coating protein. The env gene encodes a precursor glycoprotein which is cleaved into two glycoproteins: the extracellular protein gp120 and the transmembrane protein gp41.

Oligonucleotides targeted to a protein encoded for by mRNA which is part of a precursor protein may also be able to inhibit another protein which is also part of the precursor protein, particularly a downstream proteins. Additionally, any interference with the normal lifetime of an HIV mRNA could disrupt expression of all associated cistrons.

Oligonucleotides containing a nucleic acid sequence of SEQ. ID. NO. 13, or a nucleic acid sequence substantially corresponding to SEQ. ID. NO. 13 have a nucleic acid sequence analogous to an HIV gag nucleic acid sequence. Such oligonucleotides may inhibit HIV nucleic acid packaging into virions.

Oligonucleotides targeted to lys-tRNA may act as competitive inhibitors to lys-tRNA and, thereby, inhibit HIV reverse transcriptase activity and decrease HIV complementary DNA (cDNA) nucleic acid synthesis. lys-tRNA is used as a primer for HIV cDNA nucleic acid synthesis. Oligonucleotides targeted to lys-tRNA are designed to resemble tRNA annealed to HIV genomic RNA. Such oligonucleotides contain four regions (5' to 3'): 1) an HIV non-complementary sense region; 2) a "complementary" sense region; 3) a non-complementary loop region; and 4) an HIV complementary region. Regions 2 and 4 are substantially complementary, preferably perfectly complementary to each other and form a based-paired stem structure. The length of the based-paired stem structure should be chosen to optimize the ability of the oligonucleotide to inhibit HIV reverse transcriptase activity. The length of the base-paired stem correlating with strongest inhibition of HIV reverse transcriptase can be determined by routine experimentation. An example, of an oligonucleotide targeted to lys-tRNA is provided by an oligonucleotide consisting of the nucleic acid sequence of SEQ. ID. NO. 10. A SEQ. ID. NO. 10 oligonucleotide has a seven base non-complementary sense region, a 22 base "complementary" sense region, a four base non-complementary loop region, and a 15 base complementary region.

RRE is involved in promoting transport of env and unspliced mRNA by the Rev protein. RRE is the Rev-response element. Oligonucleotides targeted to RRE nucleic acid sequence regions are expected to inhibit such transport.

As discussed above, complementary oligonucleotides are designed to hybridize to a target sequence. The necessary degree of complementarity for hybridization will be affected by factors such as the segment length of contiguous complementary bases, the type of bases involved in hydrogen bonding (e.g., G:C hydrogen bond formation is stronger that A:T), internal additions or deletions, and structural chemical modification of the oligonucleotide.

Oligonucleotides designed to hybridize to a particular sequence should be designed to have an appropriate melting temperature ($T_m$) (the temperature at which 50% of the oligonucleotide is hybridized to its target nucleic acid). The appropriate $T_m$ can be obtained by varying the probe length and nucleotide composition (percentage of G+C versus A+T). The probe length and nucleotide composition should result in a $T_m$ about 2°–10° C. higher than physiological temperature (37° C.).

The longer the complementary region of an oligonucleotide, the more hydrogen bonding to a target sequence, and in general, the higher the $T_m$. Increasing the percentage of G and C also increases the $T_m$ because G-C base pairs exhibit additional hydrogen bonding and therefore greater thermal stability than A-T base pairs. $T_m$ can be determined using techniques known in the art such as measuring hybridization by the hybridization protection assay (HPA) according to Arnold et al., entitled "Homogeneous Protection Assay," EPO application number 88308767.8, publication number 309230, and Nelson et al., in *Nonisotopic DNA Probe Techniques*, p. 275 Academic Press, San Diego (Kricka, ed., 1992) (these references are hereby incorporated by reference herein). Oligonucleotides can be labeled with acridinium ester derivatives as described by Arnold, et al., PCT/US88/03361, entitled "Acridinium Ester Labeling and Purification of Nucleotide Probes," hereby incorporated by reference herein.

$T_m$ can be measured using HPA in the following manner. Oligonucleotides are labeled with an acridinium ester. Oligonucleotide:target hybrids are formed in a lithium succinate buffer (0.1M lithium succinate buffer (pH 5.0), 2 mM EDTA, 2 mM EGTA, 10% (w/v) lithium lauryl sulfate) using an excess amount of HIV RNA target. Aliquots of the solution containing the nucleic acid hybrids are then diluted in the lithium succinate buffer solution. The aliquots are incubated for five minutes at various temperatures starting below that of the anticipated $T_m$ and increasing in 2°–5° C. increments. This solution is then diluted with a mild alkaline borate buffer (0.15M sodium tetraborate, (pH 7.6), 5% (v/v) TRITON® X-100) and incubated at a lower temperature for ten minutes. Under these conditions acridinium esters attached to single-stranded oligonucleotides are hydrolyzed, while acridinium esters attached to hybridized oligonucleotides are relatively protected from hydrolysis. Thus, the amount of acridinium esters remaining after hydrolysis treatment is proportional to the number of hybrid molecules present in the sample. The remaining acridinium esters can be measured by monitoring the chemiluminescence produced by addition of hydrogen peroxide and alkali to the solution. Chemiluminescence can be measured in a luminometer (e.g., the Gen-Probe LEADER® I or LEADER® 50). The resulting data is plotted as percent of maximum signal (usually from the lowest temperature) versus temperature. In this assay, the $T_m$ is determined to be the temperature at which 50% of the maximum signal remains. In addition to the method above, $T_m$ may be determined by isotopic methods well known to those skilled in the art (see e.g., Hogan et al., supra).

The oligonucleotide can also be screened by an oligonucleotide screening assay designed to mimic physiological conditions to some extent, in order to obtain a measure of the hybridization expected to occur under physiological conditions. Due to the complexity of physiological conditions, the oligonucleotide screening assay provides an approximation, rather than an exact duplication, of actual hybridization behavior in a cell. An oligonucleotide screening assay can be carried out using a DNA oligonucleotide, a corresponding acridinium ester labeled oligonucleotide, and an enzyme having RNase H activity. The assay measures the ability of the DNA oligonucleotide to hybridize to an RNA target forming an DNA:RNA duplex by measuring the subsequent degradation of the target RNA by RNAse H activity. The acridinium ester labeled oligonucleotide is used to detect remaining target nucleic acid sequence.

An oligonucleotide screening assay can be carried out as follows:

1) Hybridize oligonucleotides to their target nucleic acids in a solution, such as an aqueous physiological buffer. An example of a target nucleic acid is purified HIV mRNA. Hybridization can be carried out using 0.9 pmol of target mRNA, 0.1 pmol acridinium ester-labeled probe, in 100 μL of a physiological buffer, at 37° C. for 2 hours. The reactions are divided to make duplicates at 1×final buffer concentration for optimal RNAse H enzyme activity.

2) *E. coli* RNase H (Life Technologies, Gaithersburg, Md., 0.4 U/reaction) is added to one of the two duplicate reactions. The other duplicate reaction lacks RNase H and serves as the (−) RNase H control. The reactions are incubated at 37° C. for 1 hour, stopped by denaturing at 95° C. for 5 minutes, and placed directly on ice.

3) Aliquots of the reactions are hybridized with the appropriate phosphodiester acridinium ester-probe. Appropriate acridinium ester-probes can hybridize to the same nucleic acid sequence as the test oligonucleotide and contain an acridinium ester in the complementary region. The acridinium ester-probe is hybridized at 60° C. for 1 hour. Control hybridizations are performed using acridinium ester-probes expected to hybridize to a region other than the target nucleic acid sequence.

4) Aliquots are diluted in hybridization buffer (0.1M lithium succinate buffer (pH 5.0), 2 mM EDTA, 2 mM EGTA, 10% (w/v) lithium lauryl sulfate). Fifty microliter replicates are hydrolyzed in 12×75 mm luminometer tubes with 300 μL of 0.15M sodium tetraborate (pH 7.6), 5% (v/v) TRITON® X-100 at 60° C. until non-hybridized labeled probes are fully hydrolyzed (usually 6–8 minutes). Chemiluminescence is brought about using a single injection of 1.5N NaOH, 0.1% $H_2O_2$ and measured in a luminometer.

As would be appreciated by one skilled in the art, variations of this procedure can be performed. For example, the assay can be carried out using different amounts of reagents and incubation times.

B. Therapeutic Use

The preferred use of anti-HIV oligonucleotides is in the treatment of patients infected with HIV. By inhibiting the propagation of HIV, symptoms associated with AIDS can be delayed and/or eliminated. Considerations for therapeutic use include oligonucleotide pharmacology, mode of administration, disease stage and interaction with other drugs. These considerations are interrelated, for example, the mode of administration affects oligonucleotide pharmacology.

1. Pharmacology

Pharmacological considerations include toxicology, pharmacokinetics, absorption, distribution, metabolism and excretion. These considerations relate to the ability of the anti-HIV oligonucleotide to reach its target site, inhibit HIV propagation and to produce side effects adversely affecting patients. Different pharmacological considerations can be evaluated using techniques known in the art and described herein.

Anti-HIV oligonucleotides can effectively function as therapeutic agents by inhibiting viral propagation without gravely affecting the patient. In use as a therapeutic, it is possible there will be some adverse side effects. An overall therapeutic effect can be obtained by providing an overall benefit to the patient, such as increased life expectancy or increased responsiveness of the immune system. Adverse side effects can be reduced using standard medical techniques and include considerations such as dosage regime. For example, anti-HIV oligonucleotides having a low therapeutic index can be used at lower concentrations over a continuous time period.

Anti-HIV oligonucleotides which inhibit HIV nucleic acid to the same extent that they inhibit essential cellular functions are less preferred embodiments of the present invention. Such oligonucleotides may be able to act as a therapeutic by being delivered to only HIV infectedrecogn (e.g., using liposomes containing recognition molecules targeted to HIV infected cells).

Oligonucleotide toxicity can be evaluated before therapeutic administration using models such as cellular assays and test animals. Cellular assays can be used to measure the cytotoxic effect of an agent and its ability to inhibit HIV propagation. (For example, see Weislow et al., *J Natl Cancer Inst* 81:577–586 (1989) and the techniques described in the examples below.) Preferably, test animals are used to measure the toxicity of anti-HIV oligonucleotides.

2. Administration

Anti-HIV oligonucleotides may be introduced to the patient in different forms such naked oligonucleotide, through expression vectors (encoding such anti-HIV), or included in physiologically acceptable formulations. Pharmacologically suitable methods of delivery include using liposomes, release vehicles, iontophoresis, ion-paired molecules, and covalently attached adducts.

Different types of delivery strategies are useful in the present invention, including oligonucleotide modifications, particle carrier drug delivery vehicles, and retroviral expression vectors. Anti-HIV oligonucleotides joined by phosphodiester linkages are slowly taken up by cells. To enhance cellular uptake, the anti-HIV oligonucleotide may be modified at the phosphodiester linkage for example, the individual nucleotides may be joined by phosphorothioate or methylphosphonate linkages. Such modifications can also serve to reduce oligonucleotide susceptibility to nuclease degradation.

An expression vector encoding an anti-HIV oligonucleotide can be used to produce the oligonucleotide inside a cell. For example, Rhodes and James *Journal of General Virology* 71:1965–1975, 1990 (hereby incorporated by reference herein) describe using a vector to produce RNA which functions as an antisense oligonucleotide. A possible disadvantage of using an expression vector in therapeutic treatment is that the RNA thereby produced would not contain phosphorothioate linkages.

Anti-HIV oligonucleotides can be used to treat HIV patients using different formulations and routes of administration. Suitable routes of administration include intramuscular, aerosol, oral (tablet or pill form), topical, systemic, ocular, intraperitoneal and intrathecal.

Drug delivery vehicles can be chosen for both systemic and topical administration. Such vehicles can be designed to serve as a slow release reservoir or to deliver their contents directly to the target cell. An advantage of using direct delivery drug vehicles is that multiple molecules are delivered per uptake. Such vehicles can increase the circulation half-life of drugs which would otherwise be rapidly cleared from the blood stream. Examples of specialized drug delivery vehicles are liposomes, hydrogels, cyclodextrins, biodegradable nanocapsules, and bioadhesive microspheres.

Liposomes are hollow spherical vesicles composed of lipids arranged similarly to the lipids making up the cell membrane. They have an internal hydrophilic space for entrapping water soluble compounds and may range in size from 0.05 to several microns in diameter.

The use of liposomes as a drug delivery offers several advantages. References describing the use of liposomes as vehicles to deliver nucleic acids include Sullivan et al., *Antisense Research and Development* 2:187–197 (1992), and Juliano and Akhtar, *Antisense Research and Development* 2:165–176 (1992). Liposomes may be useful for increasing intracellular stability, uptake efficiency and biological activity. Other advantages of using liposomes include the following: they are non-toxic and biodegradable in composition; they display long circulation half-lives; and recognition molecules can be readily attached to their surface for targeting to tissues.

Anti-HIV oligonucleotides may be systemically administered. Systemic absorption refers to the accumulation of drugs in the blood stream followed by distribution throughout the body. Administration routes leading to systemic absorption include: intravenous, subcutaneous, intraperitoneal, intranasal, intrathecal and ophthalmic. Each of these administration routes expose accessible diseased cells to anti-HIV oligonucleotides. Subcutaneous administration drains into a localized lymph node which proceed through the lymphatic network into the circulation. The rate of entry into the circulation is principally a function of molecular weight or size. The use of a liposome or other drug carrier can localize the anti-HIV oligonucleotide at the lymph node. The anti-HIV oligonucleotide can be modified to diffuse into the cell, or the liposome can directly participate in the delivery of either the unmodified or modified anti-HIV oligonucleotide to the cell.

A liposome formulation which can associate anti-HIV oligonucleotides with the surface of lymphocytes and macrophages is also useful. This provides enhanced delivery to HIV-infected cells by taking advantage of the specificity of macrophage and lymphocyte immune recognition of infected cells.

Intraperitoneal administration also leads to entry into the circulation. The molecular weight or size of the oligonucleotide-delivery vehicle complex controls the entry rate.

Establishment of therapeutic levels of anti-HIV oligonucleotides within the cell depends upon the competing rates of cellular uptake versus efflux and degradation. Decreasing the degree of degradation prolongs the intracellular half-life of the anti-HIV oligonucleotide. Thus, preferred anti-HIV oligonucleotides are modified to increase their resistance to nuclease degradation and increase cellular uptake.

The exact dosage and number of doses depends upon the efficacy data from clinical trials. Several factors such as the delivery vehicle, disease indication, route of administration, and oligonucleotide stability affect the dosage. The expected dosage is between 0.001–200 mg/kg of body weight/day. The duration of treatment will extend through the course of the disease symptoms. Multiple daily doses are anticipated for topical applications, ocular applications and vaginal applications.

C. HIV Protection Assay

Anti-HIV oligonucleotides can also be used in assays measuring the ability of the oligonucleotide to inhibit HIV cytopathic effects. These assays have various uses including use to identify or confirm the presence of HIV as a disease causing agent in a person, use to determine which oligonucleotide to administer to a patient, and use to evaluate the initial effectiveness of an oligonucleotide (see Example 5, infra).

An HIV protection assay can be carried using anti-HIV oligonucleotides and standard techniques measuring cell growth. Techniques measuring cell growth include the use of dyes such as XTT (2,3-bis[2-methoxy-4-nitro-5-sulfophenyl]-2H-tetrazolium-5-carboxanilide) to measure the cells metabolic state, the use of radioactive or modified nucleotide precursors such as BUdR (bromodeoxyuradine) to measure nucleic acid replication, and the use of oligonucleotides complementary to host nucleic acids to measure production of host nucleic acids.

Assays involving host complementary oligonucleotides to measure cell growth can be carried out using an oligonucleotide containing a detectable label such as fluorescent, chemi luminescent, enzyme or radioactive label. Oligonucleotides can be designed to hybridize to host nucleic acid sequence regions such as those present in DNA, mRNA or rRNA. Examples of such nucleotide sequence regions are known in the art and can be obtained by standard techniques. The preferred source of host target nucleic acids is rRNA. A nucleic acid having a nucleotide sequence characteristic of rRNA is generally present in a cell in much greater abundance than a nucleic acid sequence present in mRNA.

HIV infects cells containing a CD4 antigen (CD4+). The major target sites are T-helper lymphocytes and cells of the monocyte/macrophage lineage. The HIV-protection assay can be performed on such cells from persons suspected of being infected with HIV. The assay can be preformed directly on such cells, or can be preformed using lysates obtained from CD4+ cells. The lysate can be used to infect cells more susceptible to HIV cytopathic effect than the isolated cells.

An HIV protection assay can be carried out as follows:

1) Isolate cells CD4+ cells from a person. Preferred cells are T-lymphocytes.

2) Incubate cells under conditions compatible with cell growth in the presence (treated cells) and absence (control cells) of an anti-HIV oligonucleotide. Examples of conditions compatible with cell growth are described by S. Gartner and M. Popovic, 1990, Virus Isolation and Production, pp. 53–70 in *Techniques in HIV Research*, ed. by A. Alaldocini and B. D. Walker. Stockton Press. New York.

3) Measure the growth of the treated and control cells at one or more time point after exposure of cells to the anti-HIV oligonucleotide.

Normal growth of control cells indicate the absence of a viral infection such as an HIV infection. Normal growth can be determined by comparing the growth of the control cells to the same type of cells which are known to be healthy.

Less than normal growth of control cells indicates the presence of some cellular disorder, such as HIV. The ability of an anti-HIV oligonucleotide to protect against HIV cytotoxicity in treated cells indicates that the disorder is due to HIV and the tested anti-HIV oligonucleotide can be used to treat the patient. Due to the variability in nucleic acid sequences of different strains of HIV, the inability of an anti-HIV oligonucleotide to inhibit HIV cell toxicity in this assay may at times fail to indicate correctly the presence of HIV. Thus, an HIV protection assay should be used along with other assays known in the art to detect the presence of HIV. Patients determined to be infected with HIV by other HIV detection assays, but not by the HIV protection assay, should be retested using the HIV protection assay in conjunction with a different oligonucleotide.

II. DETECTION OF HIV BY OLIGONUCLEOTIDE HYBRIDIZATION

Oligonucleotides targeted to HIV nucleic acids can also be used as detection probes to measure the presence of an HIV target sequence and as amplification primers to selectively amplify HIV nucleic acid. Hybridization to either the target nucleic acid or a nucleotide sequence region complementary to the target sequence is useful for detecting the presence of HIV. Production of nucleic acids having nucleotide sequences complementary to a target nucleic acid can be obtained using the target nucleic acid as a template in amplification reactions such as polymerase chain reaction (PCR) or transcription mediated amplification methods (e.g., Kacian and Fultz, entitled "Nucleic Acid Amplification Methods," EPO application number 90307503.4.

Useful guidelines for designing probes for HIV detection and amplification primers are described herein and include considerations discussed in section I.A. infra, relating to hybridization of an oligonucleotide to its complementary sequence. The considerations in section I.A should be considered in light of the different hybridization conditions under which the oligonucleotides operate. Anti-HIV oligonucleotides are used under physiological conditions. In contrast, amplification and detection probes can be used under a wider range of conditions, and are preferably used under stringent hybridization assay conditions.

A target nucleotide sequence region present on a nucleic acid molecule is amplified using a primer 5' of the target nucleotide sequence region and a primer 3' of the target nucleotide sequence region. The optimal sites for amplifying a nucleic acid sequence are conserved nucleotide sequence regions greater than about 15 bases in length, within about 350 bases, and preferably within 150 bases, of contiguous sequence. Amplification primers are designed to hybridize to these regions. A promoter can be attached to the primer for transcription mediated amplification.

The degree of amplification observed with a set of primers or promotor/primers depend on several factors, including the ability of the oligonucleotide to hybridize to its complementary sequence region and to be extended enzymatically. Because the extent and specificity of hybridization reactions are affected by several factors, manipulation of those factors determines the exact sensitivity and specificity in which a particular oligonucleotide hybridizes to its target, whether or not it is perfectly complementary to its target. The importance and effect of various assay conditions are known to those skilled in the art and are described in references such as Hogan et al., EPO Patent Application No. PCT/US87/03009, entitled "Nucleic Acid Probes for Detection and/or Quantitation of Non-Viral Organisms."

Oligonucleotide detection and amplification probes of a variety of lengths and base compositions may be used, however, preferred probes are between 18 to 100 nucleotides in length, more preferably 18 to 50 nucleotides in length and are sufficiently complementary to the target nucleic acid to hybridize under stringent hybridization conditions (e.g., conditions where probe oligonucleotide hybridizes to an HIV target sequence region and not to human nucleic acids or nucleic acid from other organisms). Optimal primers have target-binding regions of 18–38 bases, with a predicted $T_m$ (melting temperature) to target of about 65° C.

Oligonucleotide detection probes and amplification primers should be designed to minimize the stability of oligonucleotide:nontarget nucleic acid hybrids. The probes should be able to distinguish between target and non-target nucleotide sequence regions under stringent hybridization conditions. In designing probes, the differences in $T_m$ values between oligonucleotide:target and oligonucleotide:non-target duplexes should be as large as possible (e.g., at least 2° C. and preferably 5° C.).

The secondary structure of the probe and the target region also affects hybridization. The rate at which an oligonucleotide hybridizes to its target partly depends on the thermal stability of the secondary struc- ture of the target nucleic acid in the region complementary to the probe. Regions of the nucleic acid forming strong internal structures inhibitory to hybridization are less preferred target sites. Examples of such structures include hairpin stem-loop structures. Likewise, probes with extensive self-complementarity should be avoided. Intramolecular and intermolecular hybrids can form within a probe if there is sufficient self complementarity. Such structures can be avoided through careful probe design. Commercial computer programs are available to search for these types of interactions. Available computer programs include MacDNASIS™ 2.0 (Hitachi Software Engineering American Ltd.) and OLIGO® ver. 4.1 (National Bioscience).

An integrated genomic target nucleotide sequence region naturally occurs in a double stranded form, as does the product of the polymerase chain reaction (PCR). These double-stranded target nucleic acids inhibit probe:target hybridization. Double stranded target can be made accessible before the hybridization step using standard techniques such as heat denaturation.

The standard measurement of hybridization rate is the $C_0t_{1/2}$ which is measured as moles of nucleotide per liter times the time in seconds it takes for 50% of the nucleic acids to hybridize. Thus, it is the concentration of free probe times the time at which 50% of maximal hybridization occurs at that concentration. This value is determined by hybridizing various amounts of probe to a constant amount of target for a fixed time. The $C_0t_{1/2}$ is found graphically by standard procedure.

The degree of non-specific primer extension (primer-dimer formation or non-target copying) can affect amplification efficiency. Therefore, primers preferably have low self- or cross- complementarity, particularly at the 3' end. Long homopolymer tracts and high GC content should be avoided to reduce spurious primer extension. Commercial computer programs are available to aid in this aspect of the design. Available computer programs include MacDNA-SIS™ 2.0 (Hitachi Software Engineering American Ltd.) and OLIGO® ver. 4.1 (National Bioscience).

Once synthesized, detection probes may be labeled using well known methods. J. Sambrook, E. F. Fritsch and T. Maniatis, *Molecular Cloning*, Chapter 11 (2d ed. 1989). Useful labels include fluorescent, chemiluminescent, enzyme and radioactive groups.

III. Synthesis Of Oligonucleotides

Oligonucleotides containing phosphodiester linkages as well as modified linkages can be synthesized by procedures known in the art. For example, in *Methods In Enzymology* 154:287 (1987), Caruthers, et al. describe a procedure for synthesizing oligonucleotides containing phosphodiester linkages by standard phosphoramidite solid-phase chemistry; Bhatt, U.S. Pat. No. 5,252,723 describes a procedure for synthesizing oligonucleotides containing phosphorothioate linkages; and Klem, et al., PCT WO92/07864, describe the synthesis of oligonucleotides having different linkages including methylphosphonate linkages.

IV. Examples

Examples are provided below illustrating different aspects and embodiments of the present invention. These examples are not intended in any way to limit the disclosed invention. Rather, they illustrate methodologies which can be used to identify anti-HIV oligonucleotides having a nucleic acid sequence substantially corresponding to a preferred nucleic acid sequence and anti-HIV oligonucleotides consisting essentially of a preferred nucleic acid sequence. The examples also illustrate methodologies to further characterize anti-HIV oligonucleotides to facilitate therapeutic use.

Example 1
Measurement of Cell Proliferation

This example describes methods to measure cell proliferation and to measure the cytotoxicity of an oligonucleotide. Cell health can be monitored using different techniques such as microscopically observing the appearance of new cells and viable cell counting using trypan blue exclusion (R. I. Freshney, *Culture of Animal Cells, A Manual of Basic Techniques*, p. 257 (Wiley-Liss, New York 1994 ). Metabolic status of the cells can be determined using different techniques such as a colorometric assay measuring metabolic conversion of XTT to formazan, and a quantitative hybridization assay measuring the amount of rRNA present. Both the XTT assay results and the rRNA levels correlated strongly with viable cell number over a wide range of cell concentrations: for XTT assays ranging from at least $10^4$ to $10^6$ cells/ml; and for rRNA assays ranging from at least $10^3$ to $10^6$ cells/ml.

The following procedure ("Technique A") was used to determine cell proliferation in some of the examples described below. First, 25 µl of a 1 mg/ml 2,3-bis[2-methoxy-4-nitro-5-sulfophenyl]-2H-tetrazolium-5-carboxanilide (XTT; Sigma Chemical Co.) and 0. 025 mM phenazine methosulfate (PMS; Sigma Chemical Co.) solution was added to wells containing 100 µl of infected or uninfected cells. The treated cells were incubated at 37° C. for 4 hours in a humidified 5% $CO_2$ atmosphere. A 5% (v/v) TRITON® X-100 solution was then added to each well to obtain a final detergent concentration of 0.5%. This concentration of detergent inactivated the virus. The light absorbance of the sample in each well at 450 nm and 650 nm was determined. The absorbance at 650 nm was used to correct for light scattering due to debris in the wells. The absorbance at 450 nm, which measures formazan production due to cellular metabolism of XTT, correlated strongly with the viable cell count. Viable cell count was determined by microscopic examination in the presence of trypan blue.

Oligonucleotide cytotoxicity was determined by seeding wells of 96-well dishes with 10,000 cells/well along with various concentrations of oligonucleotides in a final volume of 0.25 ml RPMI 1640 media supplemented with 10% fetal bovine serum. The cells were incubated at 37° C. in a humidified 5% $CO_2$ atmosphere for 6 days, the contents of each well were then mixed and 100 µl was transferred to a new 96-well dish to measure cell proliferation using the XTT assay. In some experiments cell density of remaining culture was determined by viable cell counting.

The results of cytotoxicity studies using Jurkat cells are summarized in Table 2. The tested oligonucleotides were phosphorothioate oligonucleotides corresponding to a specified nucleotide sequence (i.e., consisting of the nucleotides denoted by the sequence identification number). Most of the tested oligonucleotides had no cytotoxic effect at concentrations up to 9 µm ($IC_{50}$>9). Phosphorothioate oligonucleotides corresponding to SEQ. ID. NOs. 5 and 13 had some cytotoxic effect at the high end of the tested range.

TABLE 2

| Cytotoxicity of Phosphorothioate Oligonucleotides | |
|---|---|
| Oligonucleotide | $IC_{50}$ (µM) |
| SEQ ID NO:1 | >9 |
| SEQ ID NO:2 | >9 |
| SEQ ID NO:3 | >9 |
| SEQ ID NO:5 | 7 |
| SEQ ID NO:7 | >9 |
| SEQ ID NO:8 | >9 |
| SEQ ID NO:9 | >9 |
| SEQ ID NO:11 | >9 |
| SEQ ID NO:12 | >9 |
| SEQ ID NO:13 | 5 |
| SEQ ID NO:14 | >9 |
| SEQ ID NO:15 | >9 |
| SEQ ID NO:16 | >9 |
| SEQ ID NO:17 | >9 |
| SEQ ID NO:18 | >9 |
| SEQ ID NO:19 | >9 |
| SEQ ID NO:20 | >9 |
| SEQ ID NO:21 | >9 |

TABLE 2-continued

Cytotoxicity of Phosphorothioate Oligonucleotides

| Oligonucleotide | IC$_{50}$ (µM) |
|---|---|
| SEQ ID NO:22 | >9 |
| SEQ ID NO:23 | >9 |
| SEQ ID NO:24 | >9 |
| SEQ ID NO:25 | >9 |

Additional measures of cellular cytotoxicity of anti-HIV agents can be obtained using primary human cells. For example, the colony-forming ability of hematopoietic cells in semi-solid medium has been used to evaluate the cytotoxicity of many anti-neoplastic agents. Cytotoxicity in primary human cells can be carried out, for example, using techniques B and C.

Technique B

Human bone marrow cells are harvested and washed using standard techniques. (See, e.g., *Exp. Hematol.* (Suppl. 16) 13:16–22, 1985). Cells are incubated for eight days in tissue culture medium containing 0.3% (w/v) agar, 20% (v/v) FCS (fetal calf serum) and 10 ng/ml human granulocyte-colony stimulating factor, in the presence of varying amounts of oligonucleotides. After the incubation, the number of colonies are counted.

Technique C

This method was originally developed to measure the potential for chromosome aberrations in mutagen tests (Evans et al., *Mutat. Res.* 31:135, 1975). Human lymphocytes are collected and stimulated in RPMI-1640 culture medium supplemented with 20% fetal bovine serum, 50 µg/ml gentamicin sulfate by exposure to 5 µg/ml PHA-M (phytohemagglutinin (M)) for 48 hours. Various concentrations of each oligonucleotide are added to different cultures and the cells are incubated for an additional 24 hours. The IC$_{50}$ values for inhibition of lymphocyte growth are determined and microscopic examination of metaphase chromosom is carried out.

Example 2
Measuring HIV propagation

This example describes measuring the level of HIV-1 p24 core antigen to measure HIV propagation. As described below, supernatants from cell cultures were typically frozen before assaying the p24 antigen level. Freezing allows p24 antigen level to be determined at a later time.

Frozen supernatant cultures were thawed at room temperature and diluted to various levels in fresh media. HIV-1 p24 antigen level was determined using a capture ELISA purchased from Coulter Corporation. The kinetic assay format was used and carried out according to the manufacturer's instructions.

Example 3
Acute Infection Assay

An acute infection assay format involves infection at low virus titer (low multiplicity of infection) combined with extended incubation. Multiple rounds of infection and virus replication are possible as the cell and virus populations grow concurrently. At a sufficiently low multiplicity of infection (determined by routine experimentation), production of high levels of a virus marker (e.g., p24 antigen) depends not only on virus gene expression in a single generation of infected cells, but also on production of infectious virus and additional cycles of cell infection (and possibly super-infection) during incubation. Thus, the ability of an oligonucleotide to inhibit infectious virus production as evidenced by this method is relevant to predicting therapeutic efficacy.

Oligonucleotides were tested for their ability to block acute HIV-1 infection in T-lymphocyte cell lines. Assays were conducted on Jurkat, clone E6-1 (ATCC TIB 152) and SupT-1 (Advanced BioTechnologies Inc.). Cells were propagated in RPMI 1640 media supplemented with 10% (v/v) fetal bovine serum and 50 mg/ml gentamicin sulfate at 37° C. in a humidified 5% $CO_2$ atmosphere. Only cell cultures having viable titers less than $2\times10^6$ cells/ml and viability in excess of 90%, as gauged by trypan blue exclusion, were used as hosts for acute infection.

Approximately, $3\times10^6$ cells were diluted with fresh media to a final volume of 25 ml and pelleted by centrifugation at 135×g for 8 minutes. The media was removed and the cells were gently resuspended in fresh media to a final concentration of $1\times10^6$ cells/ml. HIV-1, strain IIIB ($1\times10^5$ TCID$_{50}$/ml; TCID=Tissue Culture Infective Dose), was added to the cells to obtain a multiplicity of infection of 0.04 syncytia-forming units (sfu) per cell (0.7 sfu=1.0 TCID$_{50}$). The virus and cell mixture was incubated for 2 hours at 37° C. in a humidified 5% $CO_2$ atmosphere, and then diluted to 25 ml with media and pelleted by centrifugation at 135×g for 8 minutes. The pelleted cells were washed twice with 25 ml of media and then resuspended in media to a concentration of $8\times10^4$ cells/ml.

Cells were dispensed in 125 µl volumes to round bottom wells, of 96-well plates, containing an equal volume of media with various oligonucleotide concentrations, or media with no oligonucleotide. Each concentration of oligonucleotide was tested at least twice. The plates were incubated at 37° C. in a humidified 5% $CO_2$ atmosphere.

After 6 days, the wells were examined microscopically to approximate the total cellular mass and to count the number of syncytia. The contents of each well were then mixed by pipetting, and 100 µl of each culture was transferred to a well of a flat-bottom 96-well microtiter plate to measure cell proliferation. The remaining cells in each culture were pelleted in situ by centrifuging the incubation plate at 135×g for 8 minutes. Eighty microliters of the cleared media were transferred to a new 96-well plate and frozen at −80° C. for subsequent determination of p24 core antigen level as described in Example 2 above.

The EC$_{90}$ of different anti-HIV oligonucleotides are shown in Table 3. All of the oligonucleotides shown is Table 3 contained only phosphorothioate linkages. EC$_{90}$ refers to the concentration of oligonucleotide required to achieve 90% inhibition of p24 antigen production.

TABLE 3

Antiviral Potency of Phosphorothioate Oligonucleotides

| Oligonucleotide | Average EC$_{90}$ (nM) |
|---|---|
| SEQ ID NO:1 | 180 |
| SEQ ID NO:2 | 190 |
| SEQ ID NO:3 | 140 |
| SEQ ID NO:4 | 190 |
| SEQ ID NO:5 | 160 |
| SEQ ID NO:6 | 150 |
| SEQ ID NO:7 | 350 |
| SEQ ID NO:8 | 150 |
| SEQ ID NO:9 | 280 |
| SEQ ID NO:10 | 60 |
| SEQ ID NO:11 | 280 |
| SEQ ID NO:12 | 170 |
| SEQ ID NO:13 | 280 |

TABLE 3-continued

Antiviral Potency of Phosphorothioate Oligonucleotides

| Oligonucleotide | Average EC$_{90}$ (nM) |
| --- | --- |
| SEQ ID NO:14 | 390 |
| SEQ ID NO:15 | 270 |
| SEQ ID NO:16 | 200 |
| SEQ ID NO:17 | 190 |
| SEQ ID NO:18 | 350 |
| SEQ ID NO:19 | 1500 |
| SEQ ID NO:20 | 350 |
| SEQ ID NO:21 | 400 |
| SEQ ID NO:22 | 150 |
| SEQ ID NO:23 | 110 |
| SEQ ID NO:24 | 220 |
| SEQ ID NO:25 | 110 |

Example 4
Chronic Infection Assay

Oligonucleotides were assayed using the chronically infected human cell line 8E5 (ATCC CRL 8993). This cell line is a T-cell leukemia line containing a single proviral HIV genome (LAV-1 strain) with a single base insertion in the pol gene locus which inactivates reverse transcriptase production (Folks et al., U.S. Pat. No. 4,752,565). Since p24 production in this system is not a function of de novo infection events, this system is useful for identifying anti-HIV oligonucleotides able to inhibit HIV gene expression.

Cultures of 8E5 cells were grown in RPMI 1640 media supplemented to 10% (v/v) with fetal bovine serum and 50 mg/ml gentamicin sulfate. The cells were grown at 37° C. in a humidified 5% CO$_2$ atmosphere. Cultures having viable titers of less than 2×10$^6$ cells/ml and having viability in excess of 90%, as gauged by trypan blue exclusion, were used to initiate assays measuring the ability of an oligonucleotide to inhibit HIV-1 propagation.

Assays were carried out by first diluting cultures 1:2 with fresh media and growing overnight at 37° C., in a humidified 5% CO$_2$ atmosphere. Cells were collected by centrifugation at 135×g for 8 minutes. The media was removed, and the cells were gently resuspended with fresh media and pelleted to wash away free virus in the culture media. The cells were then resuspended in fresh media at a concentration of 8×10$^4$ cells/ml and 125 µl aliquots were dispensed to wells of a round-bottom 96-well plate containing an equal volume of media. The wells contained various oligonucleotide concentrations or had no added oligonucleotide. Each well usually contained about 10,000 infected cells. Oligonucleotides were tested at least twice at concentrations of 8 µM, 2 µM, 0.5 µM, 125 nM and 31.3 nM.

The microtiter plates were incubated at 37° C. in a humidified 5% CO$_2$ atmosphere. After 6 days, the contents of the wells were mixed by pipetting and 100 µl of each culture was transferred to a flat-bottom 96-well plate to measure cell proliferation. Cell proliferation was determined as described in Example 1, Technique A, supra.

Cells in the remaining cultures were pelleted in the 96-well plate by centrifuging the plate at 135×g for 8 minutes. Seventy-five microliters of the cleared media was transferred to a new 96-well plate and frozen at −80° C. for later p24 core antigen determination. The pelleted cells were resuspended in the remaining media and 50 µl of this cell suspension was also frozen at −80° C. for p24 core antigen determination. Antigen level was determined as described in Example 2 supra.

Figure 1B:
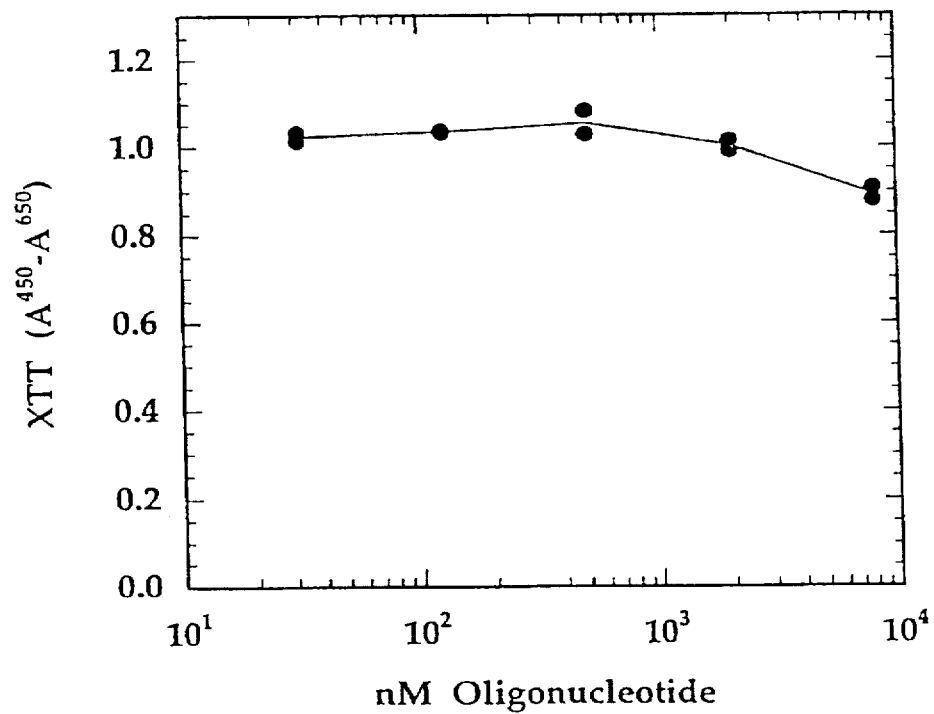
Figure 2A:
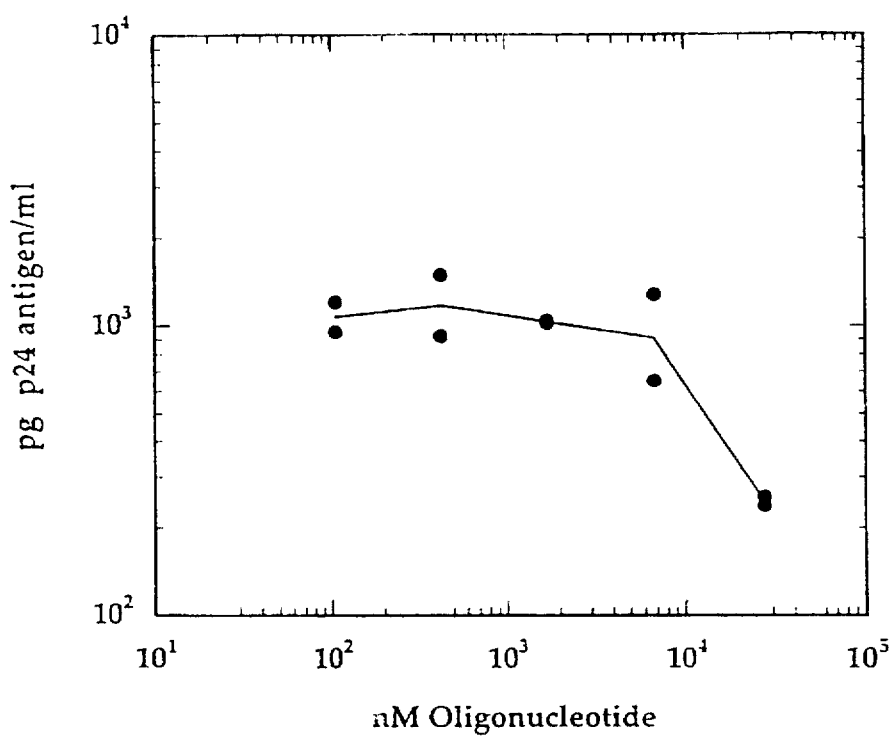
FIGS. 2A and 2B illustrate the ability of phosphorothioate oligonucleotide corresponding to SEQ. ID. NO. 3, to inhibit HIV gene expression in chronically infected cells.
Figure 2B:
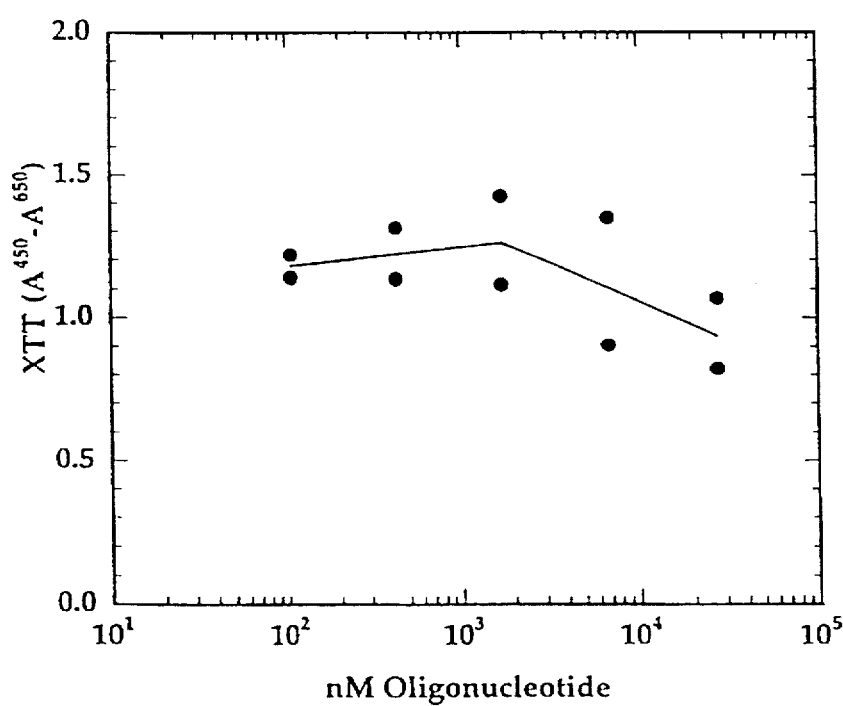
Figure 3A:
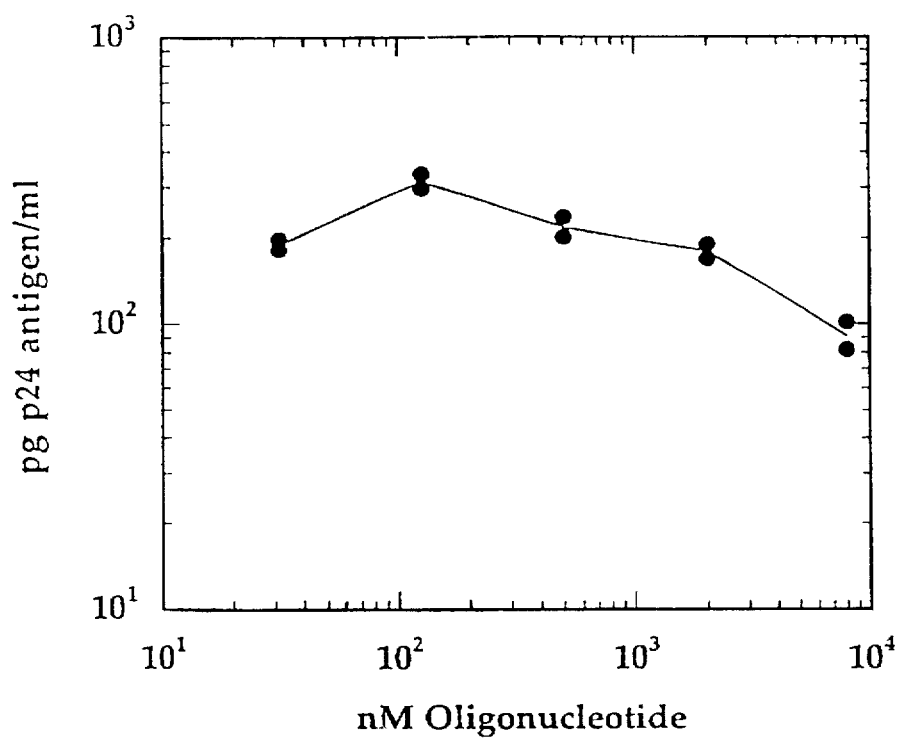
FIGS. 3A and 3B illustrate the ability of phosphorothioate oligonucleotide corresponding to SEQ. ID. NO. 8, to inhibit HIV gene expression in chronically infected cells.
Figure 3B:
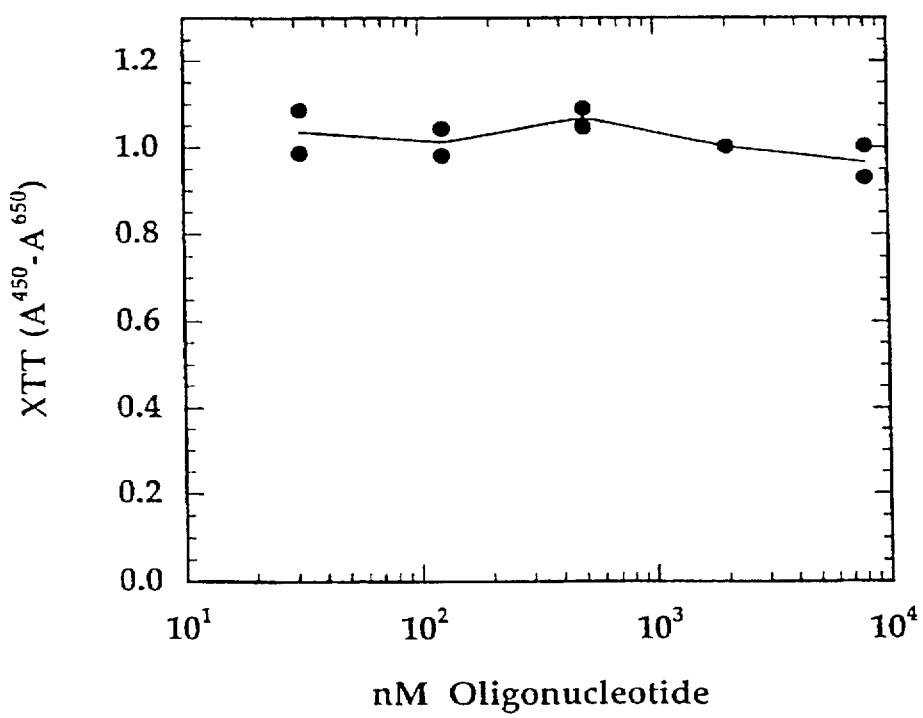

The results of this assay for phosphorothioate oligonucleotides corresponding to SEQ. ID. NOs. 2, 3, and 8 are shown in FIGS. 1, 2, and 3 respectively. The upper panels of FIGS. 1, 2, and 3 show the reduction in p24 secretion into the media from 8E5 cells resulting from treatment with anti-HIV oligonucleotides. The lower panels of these figures illustrate the cytotoxic effect. For each of the tested oligonucleotides the HIV inhibitory effect was greater the cytotoxic effect. Thus, these experiments provide further support for the therapeutic use of phosphorothioate oligonucleotide corresponding to SEQ. ID. Nos: 2, 3, and 8.

Example 5
HIV Protection Assay

This example describes the measurement of oligonucleotide anti-HIV activity by assaying the ability of the oligonucleotide to inhibit HIV cytopathic effects. Infection of certain cell lines such as SupT-1 with certain strains of HIV-1 such as the IIIB strain leads to death of the infected cells. Treatments preventing HIV growth will rescue the cells from HIV induced cytopathic effects.

Assays were conducted on SupT-1 (Advanced BioTechnologies Inc.) cells propagated in RPMI 1640 media supplemented with 10% fetal bovine serum and 50 µg/ml gentamicin sulfate at 37° C. in a humidified 5% CO$_2$ atmosphere. Only cell cultures having viable titers less than 2×10$^6$ cells/ml and viability exceeding 90%, as gauged trypan blue exclusion, were used as hosts for acute infection.

Routinely, 3×10$^6$ cells were diluted with fresh media to a final volume of 25 ml and then pelleted by centrifugation at 135×g for 8 minutes. After removal of the media, the cells were gently resuspended with fresh media to a final concentration of 1×10$^6$ cells/ml. HIV-1, strain IIIB (1×10$^5$ TCID$_{50}$/ml; TCID=Tissue Culture Infective Dose), was added to the cells to obtain a multiplicity of infection of 0.04 syncytia-forming units (sfu) per cell (0.7 sfu=1.0 TCID$_{50}$). The virus and cell mixture was incubated for 20 hours at 37° C. in a humidified 5% CO$_2$ atmosphere. After this period, the infected cells were diluted to 25 ml with media and pelleted by centrifugation at 135×g for 8 minutes. The pelleted cells were washed twice more with 25 ml volumes of media and then resuspended in media to a concentration of 8×10$^4$ cells/ml.

Cells were dispensed in 125 µl volumes to wells of round-bottom, 96-well plates that previously received an equal volume of media containing various oligonucleotide concentrations. The wells contained 10,000 infected cells/ well and the following oligonucleotide concentrations: 0, 9 µM, 3 µM, 1 µM, 333 nM, 111 nM, 37 nM 12.3 nM, 4.1 nM and 1.4 nM. All oligonucleotides were tested at least twice for each concentration. The plates were incubated at 37° C. in a humidified 5% CO$_2$ atmosphere.

After 6 days, the wells were examined microscopically to estimate the total cellular mass and number of syncytia. The contents of the wells were then mixed by pipetting and 100 µl of each culture was transferred to a flat-bottom 96-well plate for assay of cytotoxic effects using Technique A as described in Example 1. Cells in the remaining culture were pelleted in the wells by centrifuging the incubation plate at 135×g for 8 minutes. Eighty microliters of the cleared media were transferred to a new 96-well plate and frozen at −80° C. for later determination of p24 core antigen levels as described in Example 2.

Figure 4:
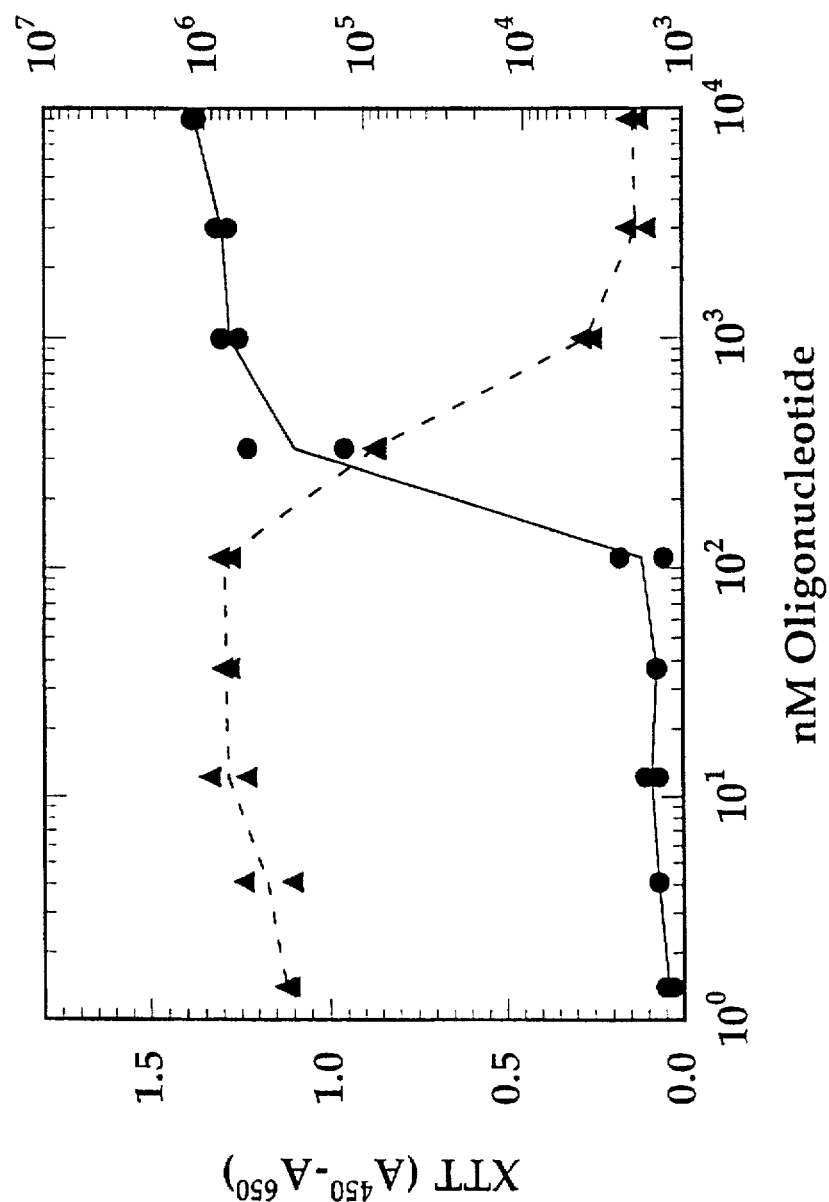
FIG. 4, shows the protection of infected cells from cytopathic HIV effects by treatment with a phosphorothioate oligonucleotide corresponding to SEQ. ID. NO. 3 and the corresponding decline in virus reduction.

FIG. 4 shows the protection of infected cells from cytopathic HIV effects by treatment with a phosphorothioate oligonucleotide corresponding to SEQ. ID. NO. 3. At oligonucleotide concentrations below 100 nM, virus production, as judged by the synthesis of p24 core antigen, occurs unabated and cell proliferation, as judged by XTT metabolism, is barely detectable. Increasing oligonucleotide concentration resulted in a 100- to 1000-fold reduction in virus production and in protecting the HIV infected cells so that cell proliferation of HIV infected cells is identical to that of uninfected cells.

Example 6
Plaque Assay for HIV Infection

This example describes measuring anti-HIV activity of oligonucleotides using a HIV plaque formation assay. HT-6C cells (clone 6C of Hela cells expressing CD4 from a recombinant retroviral vector, NIH AIDS Research and Reference Reagent Program) were maintained in 75 cm$^2$ tissue culture flasks in DMEM media (GibcoBRL) supplemented with 10% fetal bovine serum, 100 units/ml penicillin, 100 μg/ml streptomycin, 2 mM glutamine at 37° C. in a humidified 5% $CO_2$ atmosphere. The cells were detached from the flasks with trypsin-EDTA (GibcoBRL), collected by centrifugation at 230×g and resuspended in the above medium. These cells were plated at 2.5×10$^4$ cells/well in 48-well tissue culture dishes and grown overnight at 37° C. in a humidified 5% $CO_2$ atmosphere.

To initiate an assay, the media was removed from each well and 200 μl of HIV (100 to 200 plaque forming units) in DMEM media supplemented with 4% fetal bovine serum, 100 units/ml penicillin, 100 μg/ml streptomycin, 2 mM glutamine, 8 μg/ml DEAE dextran, and 0.5 μg/ml polybrene were added to each well. The dishes were incubated at 37° C. in a humidified 5% $CO_2$ atmosphere. After 2 hours, 800 μl of media containing various concentrations of oligonucleotide was added to the wells and the dishes were incubated at 37° C. in a humidified 5% $CO_2$ atmosphere for 3 days. The media from each well was then removed and 1 ml of 100% methanol was added to each well to fix the cells to the dishes. After 15 minutes, the methanol was removed and 0.5 ml of 0.3% crystal violet stain dissolved in phosphate buffered saline was added to each well. After 5 minutes, the wells were rinsed with water, drained and allowed to air dry. The number of plaques (dark staining giant cells) in each well were counted during microscopic examination of each well.

FIG. 5 shows the percent reduction in plaque formation resulting from treatment with various concentrations of a phosphorothioate oligonucleotide corresponding to SEQ ID NO:3. At concentrations greater than 300 nM, plaque formation is completely suppressed. This reduction declines as oligonucleotide concentrations decrease and plaque formation approaches that of the untreated HIV infected cells at approximately 10 nM. Table 4 summarizes the antiviral potency of a phosphorothioate oligonucleotide corresponding to SEQ ID NO:3 against six strains of HIV as determined by the plaque formation assay. Strains A018 and P022 are clinical isolates that were selected for AZT resistance.

TABLE 4

| Inhibition of Plaque Formation by Phosphorothioate SEQ ID NO:3 | |
|---|---|
| Virus Strain | $EC_{50}$ (nM) |
| LAV-1 | 80 |
| A018 - AZT Sensitive | 600 |
| A018 - AZT Resistant | 480 |
| P022 - AZT Sensitive | 150 |
| P022 - AZT Resistant | 350 |
| LAV-2 | 150 |

Example 7
Toxicology

In vivo toxicology can be carried out in test animals by examining the ability of an oligonucleotide to cause gross morphological changes in organ or blood tissue. For example, a toxicology study can be carried out as follows:

1) Oligonucleotides are injected into a test mouse by the intra-tail vein. A control mouse receives a control solution lacking oligonucleotides.
2) The effect of the tested oligonucleotides on organs, tissues, and blood parameters are measured at different time points (e.g., t=0 and at 24 hours).

Blood parameters indicative of a toxic effect include changes in the number of platelets, red blood cells, white blood cells, and hemoglobin. Examples of important organs and tissues to monitor to gauge toxic effect are spleen, liver, kidney and thymus.

Other embodiments are within the following claims.

We claim:

1. An oligonucleotide consisting of a nucleic acid sequence selected from the group consisting of: SEQ. ID. NOS: 1–18 and 20–25, wherein said oligonucleotide optionally contains one or more modified sugars and optionally contains one or more modified internucleoside linkages, and wherein said oligonucleotide inhibits HIV propagation.

2. The oligonucleotide of claim 1, wherein said oligonucleotide is optionally modified with one or more modified internucleoside linkages each independently selected from the group consisting of: phosphorothioate, methylphosphonate and phosphorodithioate; and said oligonucleotide is optionally modified with one or more 2'-O-methyloligonucleotides.

3. The oligonucleotide of claim 1, wherein said oligonucleotide is a DNA oligonucleotide optionally containing one or more modified internucleoside linkages each independently selected from the group consisting of: phosphorothioate, methylphosphonate and phosphorodithioate.

4. The oligonucleotide of claim 3, wherein said nucleic acid sequence is SEQ ID NO 1.

5. The oligonucleotide of claim 3, wherein said nucleic acid sequence is SEQ ID NO 2.

6. The oligonucleotide of claim 3, wherein said nucleic acid sequence is SEQ ID NO 3.

7. The oligonucleotide of claim 3, wherein said nucleic acid sequence is SEQ ID NO 4.

8. The oligonucleotide of claim 3, wherein said nucleic acid sequence is SEQ ID NO 5.

9. The oligonucleotide of claim 3, wherein said nucleic acid sequence is SEQ ID NO 6.

10. The oligonucleotide of claim 3, wherein said nucleic acid sequence is SEQ ID NO 7.

11. The oligonucleotide of claim 3, wherein said nucleic acid sequence is SEQ ID NO 8.

12. The oligonucleotide of claim 1, wherein said nucleic acid sequence is SEQ ID NO 9.

13. The oligonucleotide of claim 3, wherein said nucleic acid sequence is SEQ ID NO 10.

14. The oligonucleotide of claim 3, wherein said nucleic acid sequence is SEQ ID NO 11.

15. The oligonucleotide of claim 3, wherein said nucleic acid sequence is SEQ ID NO 12.

16. The oligonucleotide of claim 3, wherein said nucleic acid sequence is SEQ ID NO 13.

17. The oligonucleotide of claim 3, wherein said nucleic acid sequence is SEQ ID NO 14.

18. The oligonucleotide of claim 3, wherein said nucleic acid sequence is SEQ ID NO 15.

19. The oligonucleotide of claim 3, wherein said nucleic acid sequence is SEQ ID NO 16.

20. The oligonucleotide of claim 3, wherein said nucleic acid sequence is SEQ ID NO 17.

21. The oligonucleotide of claim 3, wherein said nucleic acid sequence is SEQ ID NO 18.

22. The oligonucleotide of claim 3, wherein said nucleic acid sequence is SEQ ID NO 20.

23. The oligonucleotide of claim 3, wherein said nucleic acid sequence is SEQ ID NO 21.

24. The oligonucleotide of claim 3, wherein said nucleic acid sequence is SEQ ID NO 22.

25. The oligonucleotide of claim 3, wherein said nucleic acid sequence is SEQ ID NO 23.

26. The oligonucleotide of claim 3, wherein said nucleic acid sequence is SEQ ID NO 24.

27. The oligonucleotide of claim 3, wherein said nucleic acid sequence is SEQ ID NO 25.

28. The oligonucleotide of any of claims 1 or 3–27, wherein at least 50% of the internucleoside linkages of said oligonucleotide are phosphorothioate linkages.

29. The oligonucleotide of claim 28, wherein all of the internucleoside linkages of said oligonucleotide are phosphorothioate linkages.

30. An oligonucleotide consisting of a sequence which may differ by a 0 to 10% base difference, excluding RNA and DNA equivalents, and which may have up to 4 additional nucleotides or up to two outside nucleotides deleted, from a nucleic acid sequence selected from the group consisting of: SEQ. ID. NOS: 3–10, 12–18, and 20–25, wherein said oligonucleotide optionally contains one or more modified sugars and optionally contains one or more modified internucleoside linkages, and wherein said oligonucleotide inhibits HIV propagation.

31. The oligonucleotide of claim 30, wherein said oligonucleotide is a DNA oligonucleotide optionally containing one or more modified internucleoside linkages each independently selected from the group consisting of: phosphorothioate, methylphosphonate and phosphorodithioate.

32. The oligonucleotide of claim 31, wherein said nucleic acid sequence is SEQ ID NO 3.

33. The oligonucleotide of claim 31, wherein said nucleic acid sequence is SEQ ID NO 4.

34. The oligonucleotide of claim 31, wherein said nucleic acid sequence is SEQ ID NO 5.

35. The oligonucleotide of claim 31, wherein said nucleic acid sequence is SEQ ID NO 6.

36. The oligonucleotide of claim 31, wherein said nucleic acid sequence is SEQ ID NO 7.

37. The oligonucleotide of claim 31, wherein said nucleic acid sequence is SEQ ID NO 8.

38. The oligonucleotide of claim 31, wherein said nucleic acid sequence is SEQ ID NO 9.

39. The oligonucleotide of claim 31, wherein said nucleic acid sequence is SEQ ID NO 10.

40. The oligonucleotide of claim 31, wherein said nucleic acid sequence is SEQ ID NO 12.

41. The oligonucleotide of claim 31, wherein said nucleic acid sequence is SEQ ID NO 13.

42. The oligonucleotide of claim 31, wherein said nucleic acid sequence is SEQ ID NO 14.

43. The oligonucleotide of claim 31, wherein said nucleic acid sequence is SEQ ID NO 15.

44. The oligonucleotide of claim 31, wherein said nucleic acid sequence is SEQ ID NO 16.

45. The oligonucleotide of claim 31, wherein said nucleic acid sequence is SEQ ID NO 17.

46. The oligonucleotide of claim 31, wherein said nucleic acid sequence is SEQ ID NO 18.

47. The oligonucleotide of claim 31, wherein said nucleic acid sequence is SEQ ID NO 20.

48. The oligonucleotide of claim 31, wherein said nucleic acid sequence is SEQ ID NO 21.

49. The oligonucleotide of claim 31, wherein said nucleic acid sequence is SEQ ID NO 22.

50. The oligonucleotide of claim 31, wherein said nucleic acid sequence is SEQ ID NO 23.

51. The oligonucleotide of claim 31, wherein said nucleic acid sequence is SEQ ID NO 24.

52. The oligonucleotide of claim 31, wherein said nucleic acid sequence is SEQ ID NO 25.

53. A method of inhibiting propagation of HIV comprising the step of incubating an HIV infected cell in culture with an oligonucleotide under conditions where said oligonucleotide inhibits HIV propagation, wherein said oligonucleotide consists of a nucleic acid sequence selected from the group consisting of SEQ. ID. NOS: 1–18 and 20–25, and wherein said oligonucleotide optionally contains one or more modified sugars and optionally contains one or more modified internucleoside linkages.

54. The method of claim 53, wherein said oligonucleotide is optionally modified with one or more modified internucleoside linkages each independently selected from the group consisting of: phosphorothioate, methylphosphonate and phosphorodithioate; and said oligonucleotide is optionally modified with one or more 2'-O-methyloligonucleotides.

55. The method of claim 53, wherein said oligonucleotide is a DNA oligonucleotide optionally containing one or more modified internucleoside linkages each independently selected from the group consisting of: phosphorothioate, methylphosphonate and phosphorodithioate.

56. The method of claim 55, wherein said nucleic acid sequence is SEQ ID NO 1.

57. The method of claim 55, wherein said nucleic acid sequence is SEQ ID NO 2.

58. The method of claim 55, wherein said nucleic acid sequence is SEQ ID NO 3.

59. The method of claim 55, wherein said nucleic acid sequence is SEQ ID NO 4.

60. The method of claim 55, wherein said nucleic acid sequence is SEQ ID NO 5.

61. The method of claim 55, wherein said nucleic acid sequence is SEQ ID NO 6.

62. The method of claim 55, wherein said nucleic acid sequence is SEQ ID NO 7.

63. The method of claim 55, wherein said nucleic acid sequence is SEQ ID NO 8.

64. The method of claim 55, wherein said nucleic acid sequence is SEQ ID NO 9.

65. The method of claim 55, wherein said nucleic acid sequence is SEQ ID NO 10.

66. The method of claim 55, wherein said nucleic acid sequence is SEQ ID NO 11.

67. The method of claim 55, wherein said nucleic acid sequence is SEQ ID NO 12.

68. The method of claim 55, wherein said nucleic acid sequence is SEQ ID NO 13.

69. The method of claim 55, wherein said nucleic acid sequence is SEQ ID NO 14.

70. The method of claim 55, wherein said nucleic acid sequence is SEQ ID NO 15.

71. The method of claim 55, wherein said nucleic acid sequence is SEQ ID NO 16.

72. The method of claim 55, wherein said nucleic acid sequence is SEQ ID NO 17.

73. The method of claim 55, wherein said nucleic acid sequence is SEQ ID NO 18.

74. The method of claim 55, wherein said nucleic acid sequence is SEQ ID NO 20.

75. The method of claim 55, wherein said nucleic acid sequence is SEQ ID NO 21.

76. The method of claim 55, wherein said nucleic acid sequence is SEQ ID NO 22.

77. The method of claim 55, wherein said nucleic acid sequence is SEQ ID NO 23.

78. The method of claim 55, wherein said nucleic acid sequence is SEQ ID NO 24.

79. The method of claim 55, wherein said nucleic acid sequence is SEQ ID NO 25.

80. The method of any of claims 53 or 55–79, wherein at least 50% of the internucleoside linkages of said oligonucleotide are phosphorothioate.

81. The method of claim 80, wherein all of the internucleoside linkages of said oligonucleotide are phosphorothioate linkages.

82. A method of inhibiting propagation of HIV comprising the step of incubating an HIV infected cell in culture with an oligonucleotide under conditions where said oligonucleotide inhibits HIV propagation, wherein said oligonucleotide is 18 to 100 nucleotides in length and comprises a sequence having no more than a 10% nucleotide base difference, excluding RNA and DNA equivalents, from a nucleic acid sequence selected from the group consisting of: SEQ. ID. NOS: 3–10, 12–18, and 20–25, and wherein said oligonucleotide optionally contains one or more modified sugars and optionally contains one or more modified internucleoside linkages.

83. The method of claim 82, wherein said oligonucleotide is a DNA oligonucleotide optionally containing one or more modified internucleoside linkages each independently selected from the group consisting of: phosphorothioate, methylphosphonate and phosphorodithioate.

84. The method of claim 83, wherein said nucleic acid sequence is SEQ ID NO 3.

85. The method of claim 83, wherein said nucleic acid sequence is SEQ ID NO 4.

86. The method of claim 83, wherein said nucleic acid sequence is SEQ ID NO 5.

87. The method of claim 83, wherein said nucleic acid sequence is SEQ ID NO 6.

88. The method of claim 83, wherein said nucleic acid sequence is SEQ ID NO 7.

89. The method of claim 83, wherein said nucleic acid sequence is SEQ ID NO 8.

90. The method of claim 83, wherein said nucleic acid sequence is SEQ ID NO 9.

91. The method of claim 83, wherein said nucleic acid sequence is SEQ ID NO 10.

92. The method of claim 83, wherein said nucleic acid sequence is SEQ ID NO 12.

93. The method of claim 83, wherein said nucleic acid sequence is SEQ ID NO 13.

94. The method of claim 83, wherein said nucleic acid sequence is SEQ ID NO 14.

95. The method of claim 83, wherein said nucleic acid sequence is SEQ ID NO 15.

96. The method of claim 83, wherein said nucleic acid sequence is SEQ ID NO 16.

97. The method of claim 83, wherein said nucleic acid sequence is SEQ ID NO 17.

98. The method of claim 83, wherein said nucleic acid sequence is SEQ ID NO 18.

99. The method of claim 83, wherein said nucleic acid sequence is SEQ ID NO 20.

100. The method of claim 83, wherein said nucleic acid sequence is SEQ ID NO 21.

101. The method of claim 83, wherein said nucleic acid sequence is SEQ ID NO 22.

102. The method of claim 83, wherein said nucleic acid sequence is SEQ ID NO 23.

103. The method of claim 83, wherein said nucleic acid sequence is SEQ ID NO 24.

104. The method of claim 83, wherein said nucleic acid sequence is SEQ ID NO 25.

\* \* \* \* \*

SEQUENCE LISTING ( 1 ) GENERAL INFORMATION:

( i i i ) NUMBER OF SEQUENCES: 101

( 2 ) INFORMATION FOR SEQ ID NO: 1:

( i ) SEQUENCE CHARACTERISTICS:
( A ) LENGTH: 26
( B ) TYPE: nucleic acid
( C ) STRANDEDNESS: single
( D ) TOPOLOGY: linear ( i i ) SEQUENCE DESCRIPTION: SEQ ID NO: 1:

ATTCCTTTGT GTGCTGGTAC CCATGC                26

( 2 ) INFORMATION FOR SEQ ID NO: 2:

( i ) SEQUENCE CHARACTERISTICS:
( A ) LENGTH: 26
( B ) TYPE: nucleic acid
( C ) STRANDEDNESS: single (D) TOPOLOGY: linear (i i) SEQUENCE DESCRIPTION: SEQ ID NO: 2:

CCTCCAATTC CTTTGTGTGC TGGTAC　　　　　　　　　　26

(2) INFORMATION FOR SEQ ID NO: 3:

(i) SEQUENCE CHARACTERISTICS:
        (A) LENGTH: 26
        (B) TYPE: nucleic acid
        (C) STRANDEDNESS: single
        (D) TOPOLOGY: linear (i i) SEQUENCE DESCRIPTION: SEQ ID NO: 3:

GCTGGTGATC CTTTCCATCC CTGTGG　　　　　　　　　　26

(2) INFORMATION FOR SEQ ID NO: 4:

(i) SEQUENCE CHARACTERISTICS:
        (A) LENGTH: 25
        (B) TYPE: nucleic acid
        (C) STRANDEDNESS: single
        (D) TOPOLOGY: linear (i i) SEQUENCE DESCRIPTION: SEQ ID NO: 4:

CTCCTTGACT TTGGGGATTG TAGGG　　　　　　　　　　25

(2) INFORMATION FOR SEQ ID NO: 5:

(i) SEQUENCE CHARACTERISTICS:
        (A) LENGTH: 26
        (B) TYPE: nucleic acid
        (C) STRANDEDNESS: single
        (D) TOPOLOGY: linear (i i) SEQUENCE DESCRIPTION: SEQ ID NO: 5:

CTACTACTCC TTGACTTTGG GGATTG　　　　　　　　　　26

(2) INFORMATION FOR SEQ ID NO: 6:

(i) SEQUENCE CHARACTERISTICS:
        (A) LENGTH: 29
        (B) TYPE: nucleic acid
        (C) STRANDEDNESS: single
        (D) TOPOLOGY: linear (i i) SEQUENCE DESCRIPTION: SEQ ID NO: 6:

CCTCTGTTAG TAACATATCC TGCTTTTCC　　　　　　　　　29

(2) INFORMATION FOR SEQ ID NO: 7:

(i) SEQUENCE CHARACTERISTICS:
        (A) LENGTH: 27
        (B) TYPE: nucleic acid
        (C) STRANDEDNESS: single
        (D) TOPOLOGY: linear (i i) SEQUENCE DESCRIPTION: SEQ ID NO: 7:

CCCACTCCAT CCAGGTCATG TTATTCC　　　　　　　　　27

(2) INFORMATION FOR SEQ ID NO: 8:

(i) SEQUENCE CHARACTERISTICS:
        (A) LENGTH: 26
        (B) TYPE: nucleic acid
        (C) STRANDEDNESS: single
        (D) TOPOLOGY: linear ( i i ) SEQUENCE DESCRIPTION: SEQ ID NO: 8:

GGTTGCTTCC TTCCTCTCTG GTACCC    26

( 2 ) INFORMATION FOR SEQ ID NO: 9:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( i i ) SEQUENCE DESCRIPTION: SEQ ID NO: 9:

CCATTCATTG TGTGGCTCCC TCTGTGG    27

( 2 ) INFORMATION FOR SEQ ID NO: 10:

( i ) SEQUENCE CHARACTERISTICS:
        ( A ) LENGTH: 41
        ( B ) TYPE: nucleic acid
        ( C ) STRANDEDNESS: single
        ( D ) TOPOLOGY: linear ( i i ) SEQUENCE DESCRIPTION: SEQ ID NO: 10:

CTAGCAGTGG CGCCCGAACA GGTTCGCCTG TTCGGGCGCC A    41

( 2 ) INFORMATION FOR SEQ ID NO: 11:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 11:

CCCCGCTTA ATACTGACGC TCTCGC    26

( 2 ) INFORMATION FOR SEQ ID NO: 12:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( i i ) SEQUENCE DESCRIPTION: SEQ ID NO: 12:

CGATCTAATT CTCCCCGCT TAATACTG    28

( 2 ) INFORMATION FOR SEQ ID NO: 13:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( i i ) SEQUENCE DESCRIPTION: SEQ ID NO: 13:

CAGTATTAAG CGGGGGAGAA TTAGATCG    28

( 2 ) INFORMATION FOR SEQ ID NO: 14:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) SEQUENCE DESCRIPTION: SEQ ID NO: 14:

CCTGTACCGT CAGCGTCATT                                    20

( 2 ) INFORMATION FOR SEQ ID NO: 15:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 15:

GTCTGGCCTG TACCGTCAGC GTCATT                             26

( 2 ) INFORMATION FOR SEQ ID NO: 16:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 16:

GCCTCAATAG CCCTCAGCAA ATTGTT                             26

( 2 ) INFORMATION FOR SEQ ID NO: 17:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 17:

ATCTTTCCAC AGCCAGGATT CTT                                23

( 2 ) INFORMATION FOR SEQ ID NO: 18:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 18:

TCCTGGATGC TTCCAGGGCT CTAGTC                             26

( 2 ) INFORMATION FOR SEQ ID NO: 19:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) SEQUENCE DESCRIPTION: SEQ ID NO: 19:

TCCTGGATGC TTCCAGGGCT C                                  21

( 2 ) INFORMATION FOR SEQ ID NO: 20:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 20:

GACTTCCTGG ATGCTTCCAG GGCTC                              25

( 2 ) INFORMATION FOR SEQ ID NO: 21:

( i ) SEQUENCE CHARACTERISTICS:
    ( A ) LENGTH: 29
    ( B ) TYPE: nucleic acid
    ( C ) STRANDEDNESS: single
    ( D ) TOPOLOGY: linear ( i i ) SEQUENCE DESCRIPTION: SEQ ID NO: 21:

CTCTCCTTTC TCCATTATCA TTCTCCCGC    29

( 2 ) INFORMATION FOR SEQ ID NO: 22:

( i ) SEQUENCE CHARACTERISTICS:
    ( A ) LENGTH: 30
    ( B ) TYPE: nucleic acid
    ( C ) STRANDEDNESS: single
    ( D ) TOPOLOGY: linear ( i i ) SEQUENCE DESCRIPTION: SEQ ID NO: 22:

CATCACCTGC CATCTGTTTT CCATAATCCC    30

( 2 ) INFORMATION FOR SEQ ID NO: 23:

( i ) SEQUENCE CHARACTERISTICS:
    ( A ) LENGTH: 31
    ( B ) TYPE: nucleic acid
    ( C ) STRANDEDNESS: single
    ( D ) TOPOLOGY: linear ( i i ) SEQUENCE DESCRIPTION: SEQ ID NO: 23:

CCTGTCTACT TGCCACACAA TCATCACCTG C    31

( 2 ) INFORMATION FOR SEQ ID NO: 24:

( i ) SEQUENCE CHARACTERISTICS:
    ( A ) LENGTH: 30
    ( B ) TYPE: nucleic acid
    ( C ) STRANDEDNESS: single
    ( D ) TOPOLOGY: linear ( i i ) SEQUENCE DESCRIPTION: SEQ ID NO: 24:

GCTACTATTG CTACTATTGG TATAGGTTGC    30

( 2 ) INFORMATION FOR SEQ ID NO: 25:

( i ) SEQUENCE CHARACTERISTICS:
    ( A ) LENGTH: 30
    ( B ) TYPE: nucleic acid
    ( C ) STRANDEDNESS: single
    ( D ) TOPOLOGY: linear ( i i ) SEQUENCE DESCRIPTION: SEQ ID NO: 25:

ACTATTGCTA TTATTATTGC TACTACTAAT    30

( 2 ) INFORMATION FOR SEQ ID NO: 26:

( i ) SEQUENCE CHARACTERISTICS:
    ( A ) LENGTH: 26
    ( B ) TYPE: nucleic acid
    ( C ) STRANDEDNESS: single
    ( D ) TOPOLOGY: linear ( i i ) SEQUENCE DESCRIPTION: SEQ ID NO: 26:

AUUCCUUUGU GUGCUGGUAC CCAUGC    26

( 2 ) INFORMATION FOR SEQ ID NO: 27:

( i ) SEQUENCE CHARACTERISTICS:
    ( A ) LENGTH: 26
    ( B ) TYPE: nucleic acid
    ( C ) STRANDEDNESS: single
    ( D ) TOPOLOGY: linear ( i i ) SEQUENCE DESCRIPTION: SEQ ID NO: 27:

CCUCCAAUUC CUUUGUGUGC UGGUAC                    26

( 2 ) INFORMATION FOR SEQ ID NO: 28:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 28:

GCUGGUGAUC CUUUCCAUCC CUGUGG                    26

( 2 ) INFORMATION FOR SEQ ID NO: 29:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 29:

CUCCUUGACU UUGGGGAUUG UAGGG                     25

( 2 ) INFORMATION FOR SEQ ID NO: 30:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 30:

CUACUACUCC UUGACUUUGG GGAUUG                    26

( 2 ) INFORMATION FOR SEQ ID NO: 31:

( i ) SEQUENCE CHARACTERISTICS:
        ( A ) LENGTH: 29
        ( B ) TYPE: nucleic acid
        ( C ) STRANDEDNESS: single
        ( D ) TOPOLOGY: linear ( i i ) SEQUENCE DESCRIPTION: SEQ ID NO: 31:

CCUCUGUUAG UAACAUAUCC UGCUUUUCC                 29

( 2 ) INFORMATION FOR SEQ ID NO: 32:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( i i ) SEQUENCE DESCRIPTION: SEQ ID NO: 32:

CCCACUCCAU CCAGGUCAUG UUAUUCC                   27

( 2 ) INFORMATION FOR SEQ ID NO: 33:

( i ) SEQUENCE CHARACTERISTICS:

( A ) LENGTH: 26
            ( B ) TYPE: nucleic acid
            ( C ) STRANDEDNESS: single
            ( D ) TOPOLOGY: linear ( i i ) SEQUENCE DESCRIPTION: SEQ ID NO: 33:

GGUUGCUUCC UUCCUCUCUG GUACCC    26

( 2 ) INFORMATION FOR SEQ ID NO: 34:

( i ) SEQUENCE CHARACTERISTICS:
            ( A ) LENGTH: 27
            ( B ) TYPE: nucleic acid
            ( C ) STRANDEDNESS: single
            ( D ) TOPOLOGY: linear ( i i ) SEQUENCE DESCRIPTION: SEQ ID NO: 34:

CCAUUCAUUG UGUGGCUCCC UCUGUGG    27

( 2 ) INFORMATION FOR SEQ ID NO: 35:

( i ) SEQUENCE CHARACTERISTICS:
            ( A ) LENGTH: 41
            ( B ) TYPE: nucleic acid
            ( C ) STRANDEDNESS: single
            ( D ) TOPOLOGY: linear ( i i ) SEQUENCE DESCRIPTION: SEQ ID NO: 35:

CUAGCAGUGG CGCCCGAACA GGUUCGCCUG UUCGGGCGCC A    41

( 2 ) INFORMATION FOR SEQ ID NO: 36:

( i ) SEQUENCE CHARACTERISTICS:
            ( A ) LENGTH: 26
            ( B ) TYPE: nucleic acid
            ( C ) STRANDEDNESS: single
            ( D ) TOPOLOGY: linear ( i i ) SEQUENCE DESCRIPTION: SEQ ID NO: 36:

CCCCCGCUUA AUACUGACGC UCUCGC    26

( 2 ) INFORMATION FOR SEQ ID NO: 37:

( i ) SEQUENCE CHARACTERISTICS:
            ( A ) LENGTH: 28
            ( B ) TYPE: nucleic acid
            ( C ) STRANDEDNESS: single
            ( D ) TOPOLOGY: linear ( i i ) SEQUENCE DESCRIPTION: SEQ ID NO: 37:

CGAUCUAAUU CUCCCCGCU UAAUACUG    28

( 2 ) INFORMATION FOR SEQ ID NO: 38:

( i ) SEQUENCE CHARACTERISTICS:
            ( A ) LENGTH: 28
            ( B ) TYPE: nucleic acid
            ( C ) STRANDEDNESS: single
            ( D ) TOPOLOGY: linear ( i i ) SEQUENCE DESCRIPTION: SEQ ID NO: 38:

CAGUAUUAAG CGGGGGAGAA UUAGAUCG    28

( 2 ) INFORMATION FOR SEQ ID NO: 39:

( i ) SEQUENCE CHARACTERISTICS:
            ( A ) LENGTH: 20
            ( B ) TYPE: nucleic acid ( C ) STRANDEDNESS: single
( D ) TOPOLOGY: linear ( i i ) SEQUENCE DESCRIPTION: SEQ ID NO: 39:

CCUGUACCGU CAGCGUCAUU                    20

( 2 ) INFORMATION FOR SEQ ID NO: 40:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 40:

GUCUGGCCUG UACCGUCAGC GUCAUU             26

( 2 ) INFORMATION FOR SEQ ID NO: 41:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 41:

GCCUCAAUAG CCCUCAGCAA AUUGUU             26

( 2 ) INFORMATION FOR SEQ ID NO: 42:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 42:

AUCUUUCCAC AGCCAGGAUU CUU                23

( 2 ) INFORMATION FOR SEQ ID NO: 43:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 43:

UCCUGGAUGC UUCCAGGGCU CUAGUC             26

( 2 ) INFORMATION FOR SEQ ID NO: 44:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) SEQUENCE DESCRIPTION: SEQ ID NO: 44:

UCCUGGAUGC UUCCAGGGCU C                  21

( 2 ) INFORMATION FOR SEQ ID NO: 45:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 45:

GACUUCCUGG AUGCUUCCAG GGCUC        25

( 2 ) INFORMATION FOR SEQ ID NO: 46:

( i ) SEQUENCE CHARACTERISTICS:
        ( A ) LENGTH: 29
        ( B ) TYPE: nucleic acid
        ( C ) STRANDEDNESS: single
        ( D ) TOPOLOGY: linear ( i i ) SEQUENCE DESCRIPTION: SEQ ID NO: 46:

CUCUCCUUUC UCCAUUAUCA UUCUCCCGC        29

( 2 ) INFORMATION FOR SEQ ID NO: 47:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO: 47:

CAUCACCUGC CAUCUGUUUU CCAUAAUCCC        30

( 2 ) INFORMATION FOR SEQ ID NO: 48:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i i ) SEQUENCE DESCRIPTION: SEQ ID NO: 48:

CCUGUCUACU UGCCACACAA UCAUCACCUG C        31

( 2 ) INFORMATION FOR SEQ ID NO: 49:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO: 49:

GCUACUAUUG CUACUAUUGG UAUAGGUUGC        30

( 2 ) INFORMATION FOR SEQ ID NO: 50:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO: 50:

ACUAUUGCUA UUAUUAUUGC UACUACUAAU        30

( 2 ) INFORMATION FOR SEQ ID NO: 51:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 51:

CTTCGGGCCT GTCGGGTCCC CTCGGG                    26

( 2 ) INFORMATION FOR SEQ ID NO:52:

( i ) SEQUENCE CHARACTERISTICS:
    ( A ) LENGTH: 26
    ( B ) TYPE: nucleic acid
    ( C ) STRANDEDNESS: single
    ( D ) TOPOLOGY: linear ( i i ) SEQUENCE DESCRIPTION: SEQ ID NO:52:

GCATGGGTAC CAGCACACAA AGGAAT                    26

( 2 ) INFORMATION FOR SEQ ID NO:53:

( i ) SEQUENCE CHARACTERISTICS:
    ( A ) LENGTH: 26
    ( B ) TYPE: nucleic acid
    ( C ) STRANDEDNESS: single
    ( D ) TOPOLOGY: linear ( i i ) SEQUENCE DESCRIPTION: SEQ ID NO:53:

GTACCAGCAC ACAAAGGAAT TGGAGG                    26

( 2 ) INFORMATION FOR SEQ ID NO:54:

( i ) SEQUENCE CHARACTERISTICS:
    ( A ) LENGTH: 26
    ( B ) TYPE: nucleic acid
    ( C ) STRANDEDNESS: single
    ( D ) TOPOLOGY: linear ( i i ) SEQUENCE DESCRIPTION: SEQ ID NO:54:

CCACAGGGAT GGAAAGGATC ACCAGC                    26

( 2 ) INFORMATION FOR SEQ ID NO:55:

( i ) SEQUENCE CHARACTERISTICS:
    ( A ) LENGTH: 25
    ( B ) TYPE: nucleic acid
    ( C ) STRANDEDNESS: single
    ( D ) TOPOLOGY: linear ( i i ) SEQUENCE DESCRIPTION: SEQ ID NO:55:

CCCTACAATC CCCAAAGTCA AGGAG                     25

( 2 ) INFORMATION FOR SEQ ID NO:56:

( i ) SEQUENCE CHARACTERISTICS:
    ( A ) LENGTH: 26
    ( B ) TYPE: nucleic acid
    ( C ) STRANDEDNESS: single
    ( D ) TOPOLOGY: linear ( i i ) SEQUENCE DESCRIPTION: SEQ ID NO:56:

CAATCCCCAA AGTCAAGGAG TAGTAG                    26

( 2 ) INFORMATION FOR SEQ ID NO:57:

( i ) SEQUENCE CHARACTERISTICS:
    ( A ) LENGTH: 29
    ( B ) TYPE: nucleic acid
    ( C ) STRANDEDNESS: single
    ( D ) TOPOLOGY: linear ( i i ) SEQUENCE DESCRIPTION: SEQ ID NO:57:

GGAAAAGCAG GATATGTTAC TAACAGAGG                 29

( 2 ) INFORMATION FOR SEQ ID NO:58:

( i ) SEQUENCE CHARACTERISTICS:
       ( A ) LENGTH: 27
       ( B ) TYPE: nucleic acid
       ( C ) STRANDEDNESS: single
       ( D ) TOPOLOGY: linear ( i i ) SEQUENCE DESCRIPTION: SEQ ID NO:58:

GGAATAACAT GACCTGGATG GAGTGGG                 27

( 2 ) INFORMATION FOR SEQ ID NO:59:

( i ) SEQUENCE CHARACTERISTICS:
       ( A ) LENGTH: 26
       ( B ) TYPE: nucleic acid
       ( C ) STRANDEDNESS: single
       ( D ) TOPOLOGY: linear ( i i ) SEQUENCE DESCRIPTION: SEQ ID NO:59:

GGGTACCAGA GAGGAAGGAA GCAACC                  26

( 2 ) INFORMATION FOR SEQ ID NO:60:

( i ) SEQUENCE CHARACTERISTICS:
       ( A ) LENGTH: 27
       ( B ) TYPE: nucleic acid
       ( C ) STRANDEDNESS: single
       ( D ) TOPOLOGY: linear ( i i ) SEQUENCE DESCRIPTION: SEQ ID NO:60:

CCACAGAGGG AGCCACACAA TGAATGG                 27

( 2 ) INFORMATION FOR SEQ ID NO:61:

( i ) SEQUENCE CHARACTERISTICS:
       ( A ) LENGTH: 41
       ( B ) TYPE: nucleic acid
       ( C ) STRANDEDNESS: single
       ( D ) TOPOLOGY: linear ( i i ) SEQUENCE DESCRIPTION: SEQ ID NO:61:

TGGCGCCCGA ACAGGCGAAC CTGTTCGGGC GCCACTGCTA G       41

( 2 ) INFORMATION FOR SEQ ID NO:62:

( i ) SEQUENCE CHARACTERISTICS:
       ( A ) LENGTH: 26
       ( B ) TYPE: nucleic acid
       ( C ) STRANDEDNESS: single
       ( D ) TOPOLOGY: linear ( i i ) SEQUENCE DESCRIPTION: SEQ ID NO:62:

GCGAGAGCGT CAGTATTAAG CGGGGG                  26

( 2 ) INFORMATION FOR SEQ ID NO:63:

( i ) SEQUENCE CHARACTERISTICS:
       ( A ) LENGTH: 28
       ( B ) TYPE: nucleic acid
       ( C ) STRANDEDNESS: single
       ( D ) TOPOLOGY: linear ( i i ) SEQUENCE DESCRIPTION: SEQ ID NO:63:

CAGTATTAAG CGGGGGAGAA TTAGATCG                28

( 2 ) INFORMATION FOR SEQ ID NO:64:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( i i ) SEQUENCE DESCRIPTION: SEQ ID NO:64:

CGATCTAATT CTCCCCCGCT TAATACTG                      28

( 2 ) INFORMATION FOR SEQ ID NO:65:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) SEQUENCE DESCRIPTION: SEQ ID NO:65:

AATGACGCTG ACGGTACAGG                                 20

( 2 ) INFORMATION FOR SEQ ID NO:66:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO:66:

AATGACGCTG ACGGTACAGG CCAGAC                        26

( 2 ) INFORMATION FOR SEQ ID NO:67:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO:67:

AACAATTTGC TGAGGGCTAT TGAGGC                        26

( 2 ) INFORMATION FOR SEQ ID NO:68:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO:68:

AAGAATCCTG GCTGTGGAAA GAT                            23

( 2 ) INFORMATION FOR SEQ ID NO:69:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO:69:

GACTAGAGCC CTGGAAGCAT CCAGGA                        26

( 2 ) INFORMATION FOR SEQ ID NO:70:

( i ) SEQUENCE CHARACTERISTICS:
    ( A ) LENGTH: 21
    ( B ) TYPE: nucleic acid
    ( C ) STRANDEDNESS: single
    ( D ) TOPOLOGY: linear ( i i ) SEQUENCE DESCRIPTION: SEQ ID NO:70:

GAGCCCTGGA AGCATCCAGG A                             21

( 2 ) INFORMATION FOR SEQ ID NO:71:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO:71:

GAGCCCTGGA AGCATCCAGG AAGTC                     25

( 2 ) INFORMATION FOR SEQ ID NO:72:

( i ) SEQUENCE CHARACTERISTICS:
        ( A ) LENGTH: 29
        ( B ) TYPE: nucleic acid
        ( C ) STRANDEDNESS: single
        ( D ) TOPOLOGY: linear ( i i ) SEQUENCE DESCRIPTION: SEQ ID NO:72:

GCGGGAGAAT GATAATGGAG AAAGGAGAG               29

( 2 ) INFORMATION FOR SEQ ID NO:73:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO:73:

GGGATTATGG AAAACAGATG GCAGGTGATG            30

( 2 ) INFORMATION FOR SEQ ID NO:74:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i i ) SEQUENCE DESCRIPTION: SEQ ID NO:74:

GCAGGTGATG ATTGTGTGGC AAGTAGACAG G          31

( 2 ) INFORMATION FOR SEQ ID NO:75:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO:75:

GCAACCTATA CCAATAGTAG CAATAGTAGC            30

( 2 ) INFORMATION FOR SEQ ID NO:76:

( i ) SEQUENCE CHARACTERISTICS:
        ( A ) LENGTH: 30

(B) TYPE: nucleic acid
    (C) STRANDEDNESS: single
    (D) TOPOLOGY: linear (ii) SEQUENCE DESCRIPTION: SEQ ID NO:76:

ATTAGTAGTA GCAATAATAA TAGCAATAGT            30

(2) INFORMATION FOR SEQ ID NO:77:

(i) SEQUENCE CHARACTERISTICS:
    (A) LENGTH: 26
    (B) TYPE: nucleic acid
    (C) STRANDEDNESS: single
    (D) TOPOLOGY: linear (ii) SEQUENCE DESCRIPTION: SEQ ID NO:77:

GCAUGGGUAC CAGCACACAA AGGAAU                26

(2) INFORMATION FOR SEQ ID NO:78:

(i) SEQUENCE CHARACTERISTICS:
    (A) LENGTH: 26
    (B) TYPE: nucleic acid
    (C) STRANDEDNESS: single
    (D) TOPOLOGY: linear (ii) SEQUENCE DESCRIPTION: SEQ ID NO:78:

GUACCAGCAC ACAAAGGAAU UGGAGG                26

(2) INFORMATION FOR SEQ ID NO:79:

(i) SEQUENCE CHARACTERISTICS:
    (A) LENGTH: 26
    (B) TYPE: nucleic acid
    (C) STRANDEDNESS: single
    (D) TOPOLOGY: linear (ii) SEQUENCE DESCRIPTION: SEQ ID NO:79:

CCACAGGGAU GGAAAGGAUC ACCAGC                26

(2) INFORMATION FOR SEQ ID NO:80:

(i) SEQUENCE CHARACTERISTICS:
    (A) LENGTH: 25
    (B) TYPE: nucleic acid
    (C) STRANDEDNESS: single
    (D) TOPOLOGY: linear (ii) SEQUENCE DESCRIPTION: SEQ ID NO:80:

CCCUACAAUC CCCAAAGUCA AGGAG                 25

(2) INFORMATION FOR SEQ ID NO:81:

(i) SEQUENCE CHARACTERISTICS:
    (A) LENGTH: 26
    (B) TYPE: nucleic acid
    (C) STRANDEDNESS: single
    (D) TOPOLOGY: linear (ii) SEQUENCE DESCRIPTION: SEQ ID NO:81:

CAAUCCCCAA AGUCAAGGAG UAGUAG                26

(2) INFORMATION FOR SEQ ID NO:82:

(i) SEQUENCE CHARACTERISTICS:
    (A) LENGTH: 29
    (B) TYPE: nucleic acid
    (C) STRANDEDNESS: single ( D ) TOPOLOGY: linear ( i i ) SEQUENCE DESCRIPTION: SEQ ID NO:82:

GGAAAAGCAG GAUAUGUUAC UAACAGAGG 29

( 2 ) INFORMATION FOR SEQ ID NO:83:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( i i ) SEQUENCE DESCRIPTION: SEQ ID NO:83:

GGAAUAACAU GACCUGGAUG GAGUGGG 27

( 2 ) INFORMATION FOR SEQ ID NO:84:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO:84:

GGGUACCAGA GAGGAAGGAA GCAACC 26

( 2 ) INFORMATION FOR SEQ ID NO:85:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( i i ) SEQUENCE DESCRIPTION: SEQ ID NO:85:

CCACAGAGGG AGCCACACAA UGAAUGG 27

( 2 ) INFORMATION FOR SEQ ID NO:86:

( i ) SEQUENCE CHARACTERISTICS:
        ( A ) LENGTH: 41
        ( B ) TYPE: nucleic acid
        ( C ) STRANDEDNESS: single
        ( D ) TOPOLOGY: linear ( i i ) SEQUENCE DESCRIPTION: SEQ ID NO:86:

UGGCGCCCGA ACAGGCGAAC CUGUUCGGGC GCCACUGCUA G 41

( 2 ) INFORMATION FOR SEQ ID NO:87:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO:87:

GCGAGAGCGU CAGUAUUAAG CGGGGG 26

( 2 ) INFORMATION FOR SEQ ID NO:88:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear (i i) SEQUENCE DESCRIPTION: SEQ ID NO:88:

CAGUAUUAAG CGGGGGAGAA UUAGAUCG                    28

(2) INFORMATION FOR SEQ ID NO:89:

(i) SEQUENCE CHARACTERISTICS:
        (A) LENGTH: 28
        (B) TYPE: nucleic acid
        (C) STRANDEDNESS: single
        (D) TOPOLOGY: linear (i i) SEQUENCE DESCRIPTION: SEQ ID NO:89:

CGAUCUAAUU CUCCCCCGCU UAAUACUG                    28

(2) INFORMATION FOR SEQ ID NO:90:

(i) SEQUENCE CHARACTERISTICS:
        (A) LENGTH: 20
        (B) TYPE: nucleic acid
        (C) STRANDEDNESS: single
        (D) TOPOLOGY: linear (i i) SEQUENCE DESCRIPTION: SEQ ID NO:90:

AAUGACGCUG ACGGUACAGG                             20

(2) INFORMATION FOR SEQ ID NO:91:

(i) SEQUENCE CHARACTERISTICS:
        (A) LENGTH: 26
        (B) TYPE: nucleic acid
        (C) STRANDEDNESS: single
        (D) TOPOLOGY: linear (i i) SEQUENCE DESCRIPTION: SEQ ID NO:91:

AAUGACGCUG ACGGUACAGG CCAGAC                      26

(2) INFORMATION FOR SEQ ID NO:92:

(i) SEQUENCE CHARACTERISTICS:
        (A) LENGTH: 26
        (B) TYPE: nucleic acid
        (C) STRANDEDNESS: single
        (D) TOPOLOGY: linear (i i) SEQUENCE DESCRIPTION: SEQ ID NO:92:

AACAAUUUGC UGAGGGCUAU UGAGGC                      26

(2) INFORMATION FOR SEQ ID NO:93:

(i) SEQUENCE CHARACTERISTICS:
        (A) LENGTH: 23
        (B) TYPE: nucleic acid
        (C) STRANDEDNESS: single
        (D) TOPOLOGY: linear (i i) SEQUENCE DESCRIPTION: SEQ ID NO:93:

AAGAAUCCUG GCUGUGGAAA GAU                         23

(2) INFORMATION FOR SEQ ID NO:94:

(i) SEQUENCE CHARACTERISTICS:
        (A) LENGTH: 26
        (B) TYPE: nucleic acid
        (C) STRANDEDNESS: single
        (D) TOPOLOGY: linear (i i) SEQUENCE DESCRIPTION: SEQ ID NO:94:

GACUAGAGCC CUGGAAGCAU CCAGGA                         26

( 2 ) INFORMATION FOR SEQ ID NO:95:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) SEQUENCE DESCRIPTION: SEQ ID NO:95:

GAGCCCUGGA AGCAUCCAGG A                              21

( 2 ) INFORMATION FOR SEQ ID NO:96:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO:96:

GAGCCCUGGA AGCAUCCAGG AAGUC                          25

( 2 ) INFORMATION FOR SEQ ID NO:97:

( i ) SEQUENCE CHARACTERISTICS:
        ( A ) LENGTH: 29
        ( B ) TYPE: nucleic acid
        ( C ) STRANDEDNESS: single
        ( D ) TOPOLOGY: linear ( i i ) SEQUENCE DESCRIPTION: SEQ ID NO:97:

GCGGGAGAAU GAUAAUGGAG AAAGGAGAG                      29

( 2 ) INFORMATION FOR SEQ ID NO:98:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO:98:

GGGAUUAUGG AAAACAGAUG GCAGGUGAUG                     30

( 2 ) INFORMATION FOR SEQ ID NO:99:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i i ) SEQUENCE DESCRIPTION: SEQ ID NO:99:

GCAGGUGAUG AUUGUGUGGC AAGUAGACAG G                   31

( 2 ) INFORMATION FOR SEQ ID NO:100:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO:100:

GCAACCUAUA CCAAUAGUAG CAAUAGUAGC                     30

( 2 ) INFORMATION FOR SEQ ID NO:101:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO:101:

```
AUUAGUAGUA  GCAAUAAUAA  UAGCAAUAGU                    30
```